(12) United States Patent
Schmidt et al.

(10) Patent No.: US 8,785,376 B2
(45) Date of Patent: Jul. 22, 2014

(54) ISOLATION, IDENTIFICATION, AND USES OF ANTIFUNGAL COMPOUNDS

(75) Inventors: Eric W. Schmidt, Salt Lake City, UT (US); Joseph O. Falkinham, Blacksburg, VA (US); Peter W. Jeffs, Chapel Hill, NC (US)

(73) Assignees: Virginia Tech Intellectual Properties, Blacksburg, VA (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/332,345

(22) Filed: Dec. 20, 2011

(65) Prior Publication Data

US 2013/0090284 A1    Apr. 11, 2013

Related U.S. Application Data

(60) Provisional application No. 61/424,994, filed on Dec. 20, 2010.

(51) Int. Cl.
*C07K 9/00* (2006.01)
*C07K 7/56* (2006.01)

(52) U.S. Cl.
CPC .................................. *C07K 9/00* (2013.01)
USPC ........................... 514/3.6; 530/322; 530/328

(58) Field of Classification Search
None
See application file for complete search history.

(56) References Cited

U.S. PATENT DOCUMENTS

| | | | |
|---|---|---|---|
| 5,232,850 A | 8/1993 | Casida, Jr. | 435/253 |
| 5,576,298 A | 11/1996 | Strobel | 514/15 |
| 6,319,497 B1 | 11/2001 | Casida, Jr. | 424/93 |
| 6,689,357 B2 | 2/2004 | Casida, Jr. | 424/93 |
| 2010/0092526 A1 | 4/2010 | Baker | 424/400 |
| 2011/0136729 A1 | 6/2011 | Lu | 514/3.6 |

FOREIGN PATENT DOCUMENTS

| | | |
|---|---|---|
| WO | WO 2011/101631 | 8/2011 |
| WO | PCT/US2012/071089 | 12/2012 |
| WO | WO 2013/096697 | 6/2013 |

OTHER PUBLICATIONS

Tawfik, Burkholdines 1097 and 1229, Potent Antifungal Peptides from *Burkholderia ambifaria* 2.2N, Organic Letters 12(4):664-666, Jan. 19, 2010.*
Dannaoui, In-vitro susceptibility of *Aspergillus* spp. Isolates to amphotericin B and itraconazole, Journal of Antimicrobial Chemotherapy 44:553-555, 1999.*
Micovic, The reduction of acid amines with lithium aluminum hydride, Communication from the Institute of Chemistry of the Serbian Academy of Sciences and the Institute of Chemistry of the Faculty of Sciences in Belgrade (Yugoslavia), Mar. 19, 1953.*
Blackburn, Chapter 11, Reactions of Alcohols, Dallas County Community College District, 2006.*
U.S. Appl. No. 61/675,802, filed Jul. 25, 2012, Eric W. Schmidt (Univ. of Utah Res. Found.).
International Search Report and Written Opinion mailed Mar. 5, 2013 for PCT/US2012/071089 filed Dec. 20, 2012 and published as WO 2013/096697 on Jun. 26, 2013 (Inventors—Schmidt et al. // Applicant—University of Utah Research Foundation) (8 pages).
Abe M, et al. (1994) Characterization of hemolytic and antifungal substance, cepalycin, from *Pseudomonas cepacia*. Microbiol Immunol. 38(1):1-9.
Bisacchi G, et al. (1987) Xylocandin: a new complex of antifungal peptides. II. Structural studies and chemical modifications. J Antibiot (Tokyo). 40(11):1520-1529.
Brautaset T, et al. (2008) Improved antifungal polyene macrolides via engineering of the nystatin biosynthetic genes in *Streptomyces noursei*. Chem Biol. 15(11):1198-1206.
Cain C, et al. (2000) Identification and characteristics of a novel *Burkholderia* strain with broad-spectrum antimicrobial activity. Appl Environ Microbiol. 66(9):4139-4141.
Casida LE, Jr. (1988) Minireview: Nonobligate bacterial predation of bacteria in soil. Microb. Ecol. 15(1):1-8.

(Continued)

*Primary Examiner* — Karlheinz R Skowronek
*Assistant Examiner* — Mindy Newman
(74) *Attorney, Agent, or Firm* — Ballard Spahr LLP

(57) ABSTRACT

In one aspect, the invention relates to isolated compounds useful as antifungal agents, for example, compounds having a structure represented by a formula:

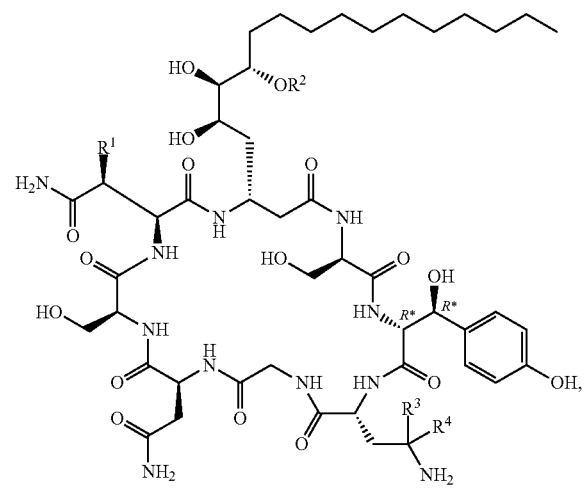

wherein $R^1$ is hydrogen or hydroxyl; wherein $R^2$ is hydrogen or xylose; and wherein $R^3$ and $R^4$ are each hydrogen or together oxygen, or a pharmaceutically acceptable salt thereof; methods of isolating and purifying same; pharmaceutical compositions comprising same; agricultural compositions comprising same; and methods of treating and/or preventing fungal infections using same. This abstract is intended as a scanning tool for purposes of searching in the particular art and is not intended to be limiting of the present invention.

23 Claims, 26 Drawing Sheets

(56) References Cited

OTHER PUBLICATIONS

Coenye T, et al. (2001) *Burkholderia ambifaria* sp. nov., a novel member of the *Burkholderia cepacia* complex including biocontrol and cystic fibrosis-related isolates. Int J Syst Evol Microbiol. 51(Pt 4):1481-1490.

Denning D, et al. (2010) Therapy for fungal diseases: opportunities and priorities. Trends Microbiol. 18(5):195-204.

Dobson, T. A., et al. (1968) Synthesis of dl-threo-and dl-erythro-β-hydroxyisoleucine. Can J Chem. 46(19):3007-3012.

Ellis D, et al. (2012) Occidiofungin's Chemical Stability and In Vitro Potency against Candida Species. Antimicrob Agents Chemother. 56(2): 765-769.

Espindola A, et al. (2009) Deconvolution of complex NMR spectra in small molecules by multi frequency homonuclear decoupling (MDEC). J Am Chem Soc. 131(44):15994-15995.

Fehlner-Gardiner C, et al. (2002) Identification of a general secretory pathway in a human isolate of *Burkholderia vietnamiensis* (formerly *B. cepacia* complex genomovar V) that is required for the secretion of hemolysin and phospholipase C activities. Microb Pathog. 32(5):249-254.

Fujii K, et al. (1997) A Nonempirical Method Using LC/MS for Determination of the Absolute Configuration of Constituent Amino Acids in a Peptide: Combination of Marfey's Method with Mass Spectrometry and Its Practical Application. Anal. Chem. 69(24):5146-5151.

Fujii K, et al. (1997) A Nonempirical Method Using LC/MS for Determination of the Absolute Configuration of Constituent Amino Acids in a Peptide: Elucidation of Limitations of Marfey's Method and of Its Separation Mechanism. Anal. Chem. 69(16):3346-3352.

Fujii K, et al. (1998). Further application of advanced Marfey's method for determination of absolute configuration of primary amino compound. Tetrahedron letters, 39(17):2579-2582.

Gross H, et al. (2009) Genomics of secondary metabolite production by *Pseudomonas* spp. Nat Prod Rep. 26(11):1408-1446.

Gu G, et al. (2009) Biosynthesis of an antifungal oligopeptide in *Burkholderia contaminans* strain MS14. Biochem Biophys Res Commun. 380(2):328-332.

Gu G, et al. (2011) Genetic and biochemical map for the biosynthesis of occidiofungin, an antifungal produced by *Burkholderia contaminans* strain MS14. Appl Environ Microbiol. 77(17):6189-6198.

Hutchison M, et al. (1998) *Burkholderia cepacia* produces a hemolysin that is capable of inducing apoptosis and degranulation of mammalian phagocytes. Infect Immun. 66(5):2033-2039.

Lim Y, et al. (1994) Cepacidine A, a novel antifungal antibiotic produced by *Pseudomonas cepacia*. II. Physico-chemical properties and structure elucidation. J Antibiot (Tokyo). 47(12):1406-1416.

Lin Z, et al. (2012) Burkholdines from *Burkholderia ambifaria*: antifungal agents and possible virulence factors. J Nat Prod. 75(9): 1518-1523.

Lu S, et al. (2009) Occidiofungin, a unique antifungal glycopeptide produced by a strain of *Burkholderia contaminans*. Biochemistry. 48(35):8312-8321.

Mahenthiralingam E, et al. (2005) The multifarious, multireplicon *Burkholderia cepacia* complex. Nat Rev Microbiol. 3(2):144-156.

Marfey P. (1984) Determination of D-amino acids. II. Use of a bifunctional reagent, 1,5-difluoro-2,4-dinitrobenzene. Carlsberg Research Communications 49(6):591-596.

McIntosh J, et al. (2010) Circular logic: nonribosomal peptide-like macrocyclization with a ribosomal peptide catalyst. J Am Chem Soc. 132(44):15499-1501.

Nakazawa T, et al. (1987) Characterization of hemolysin in extracellular products of *Pseudomonas cepacia*. J Clin Microbiol. 25(2):195-198.

Steinreiber J, et al. (2007) Overcoming thermodynamic and kinetic limitations of aldolase-catalyzed reactions by applying multienzymatic dynamic kinetic asymmetric transformations. Angew Chem Int Ed Engl. 46(10):1624-1626.

Tao J, et al. (2003) Synthesis of proposed oxidation-cyclization-methylation intermediates of the coumarin antibiotic biosynthetic pathway. Org Lett. 5(18):3233-3236.

Tawfik K, et al. (2010) Burkholdines 1097 and 1229, potent antifungal peptides from *Burkholderia ambifaria* 2.2N. Org Lett. 12(4):664-666.

Thomson E, et al. (2012) A *Burkholderia cepacia* complex non-ribosomal peptide-synthesized toxin is hemolytic and required for full virulence. Virulence. 3(3):286-298.

Vasil M, et al. (1990) Molecular analysis of hemolytic and phospholipase C activities of *Pseudomonas cepacia*. Infect Immun. 58(12):4020-4029.

Vicente M, et al. (2003) Microbial natural products as a source of antifungals. Clin Microbiol Infect. 9(1):15-32.

\* cited by examiner

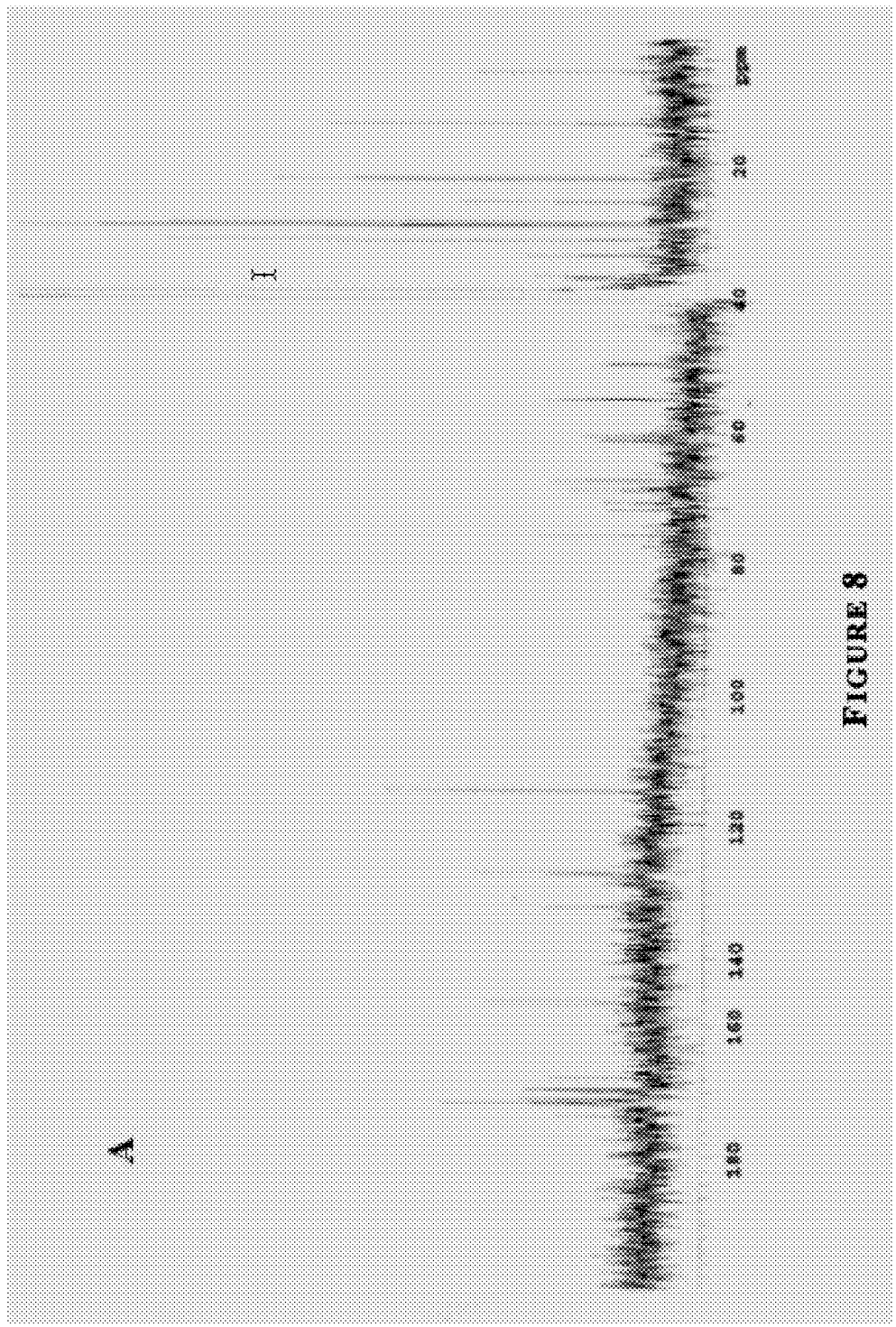

ISOLATION, IDENTIFICATION, AND USES OF ANTIFUNGAL COMPOUNDS

CROSS-REFERENCE TO RELATED APPLICATIONS

This application claims the benefit of U.S. Application No. 61/424,994 filed Dec. 20, 2010; which is hereby incorporated herein by reference in entirety.

BACKGROUND

Fungal pathogens remain a growing source of infections in plants, animals, and humans. For example, fungal infections of agricultural plants continue to impact crop growth and yield. Without effective treatments, agricultural crop yields can suffer or be destroyed. Long utilized synthetic agents have now become ineffective due increasing incidence of resistance in pathogens. While the contributions of synthetic pesticides and herbicides have proven to be of utmost value, problems of toxicity and slow degradability of these compounds in the environment is a continuing problem. To this end, alternative methods of fungal pathogen control are needed.

In mammals, incidence of superficial or cutaneous fungal infection is not uncommon. However of greater concern, the incidence of systemic fungal infections has risen significantly. Systemic fungal infections are associated with increased morbidity and mortality, especially in immuno-comprimised patients. The widespread use of antifungals in mammals has conferred increasing resistance in many pathogens.

As such, novel and alternative methods of treating fungal infections are needed. The disclosed compounds, compositions, and methods address these needs and other needs.

SUMMARY

In accordance with the purpose(s) of the invention, as embodied and broadly described herein, the invention, in one aspect, relates to compounds useful as antifungal agents, methods of isolating and purifying same, pharmaceutical compositions comprising same, agricultural compositions comprising same, and methods of treating and/or preventing fungal infections using same.

Disclosed are isolated compounds having a structure represented by a formula:

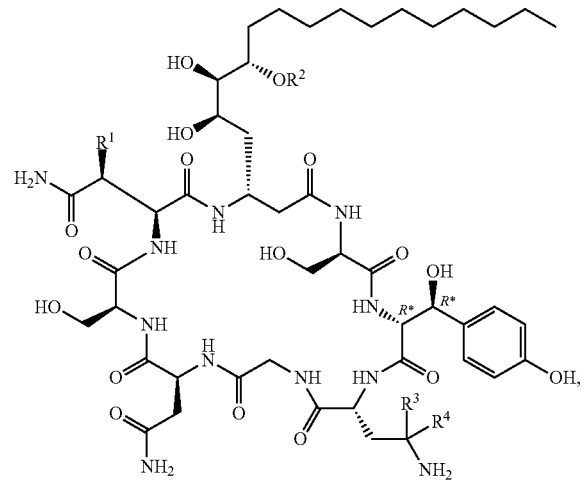

wherein $R^1$ is hydrogen or hydroxyl; wherein $R^2$ is hydrogen or xylose; and wherein $R^3$ and $R^4$ are each hydrogen or together oxygen, or a pharmaceutically acceptable salt thereof.

Also disclosed are pharmaceutical compositions comprising a compound, or a pharmaceutically acceptable salt thereof, having a structure represented by a formula:

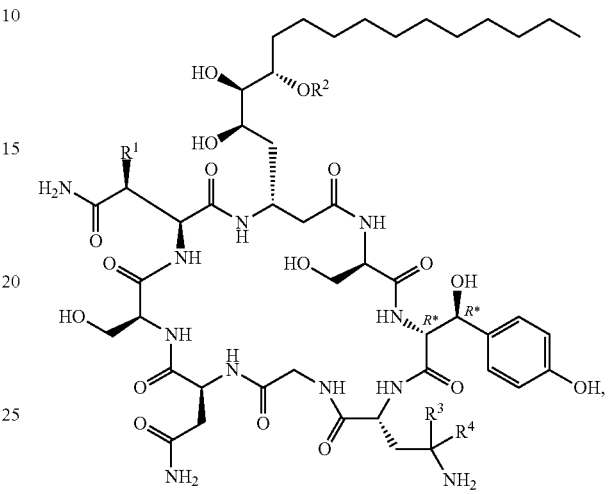

wherein $R^1$ is hydrogen or hydroxyl; wherein $R^2$ is hydrogen or xylose; and wherein $R^3$ and $R^4$ are each hydrogen or together oxygen, and a pharmaceutically acceptable carrier.

Also disclosed are methods for preparing an antifungal composition comprising combining a compound, or a pharmaceutically acceptable salt thereof, having a structure represented by a formula:

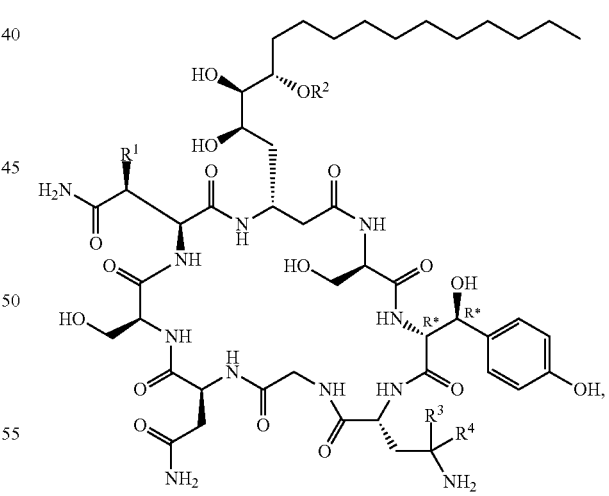

wherein $R^1$ is hydrogen or hydroxyl; wherein $R^2$ is hydrogen or xylose; and wherein $R^3$ and $R^4$ are each hydrogen or together oxygen, with a carrier.

Also disclosed are methods for the manufacture of a medicament for treatment or prevention of fungal infection in a subject, comprising combining a compound, or a pharmaceutically acceptable salt thereof, having a structure represented by a formula:

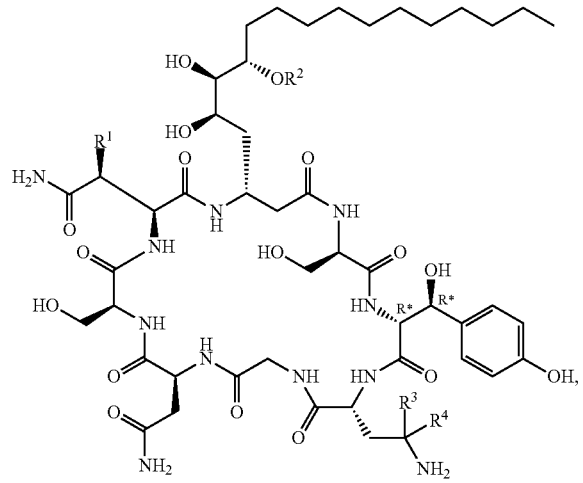

wherein R[1] is hydrogen or hydroxyl; wherein R[2] is hydrogen or xylose; and wherein R[3] and R[4] are each hydrogen or together oxygen, with a pharmaceutically acceptable carrier.

Also disclosed are methods for the manufacture of composition for treatment or prevention of fungal infection in crops, comprising combining a compound, or a agriculturally acceptable salt thereof, having a structure represented by a formula:

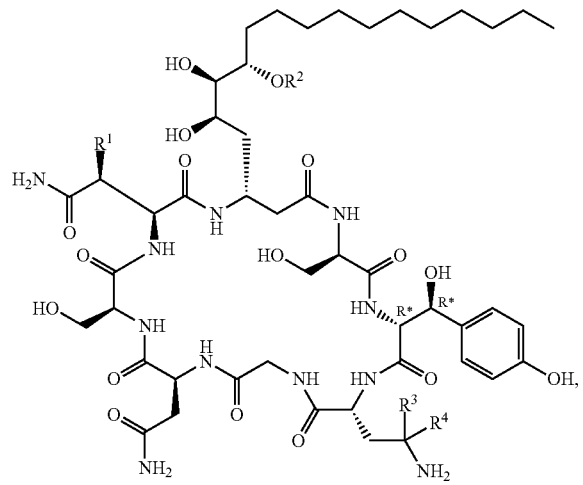

wherein R[1] is hydrogen or hydroxyl; wherein R[2] is hydrogen or xylose; and wherein R[3] and R[4] are each hydrogen or together oxygen, with an agriculturally acceptable carrier.

Also disclosed are methods for the treatment or prevention of fungal infection in a subject, comprising administering to the subject an effective amount of a compound, or a pharmaceutically acceptable salt thereof, having a structure represented by a formula:

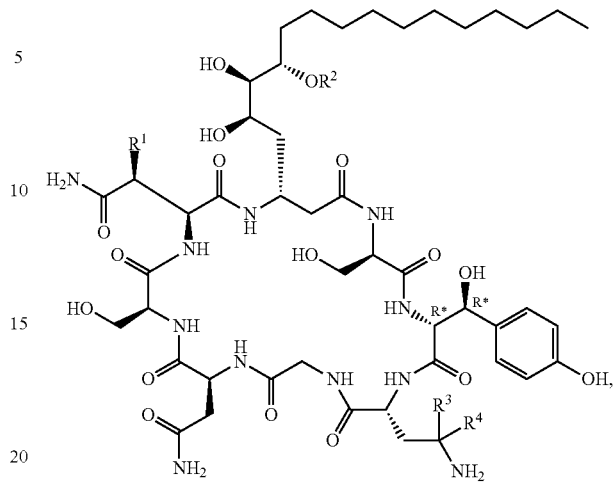

wherein R[1] is hydrogen or hydroxyl; wherein R[2] is hydrogen or xylose; and wherein R[3] and R[4] are each hydrogen or together oxygen, thereby treating or preventing of fungal infection in the subject.

Also disclosed are methods for the treatment or prevention of fungal infection in a plant, comprising administering to the plant an effective amount of a compound, or a pharmaceutically acceptable salt thereof, having a structure represented by a formula:

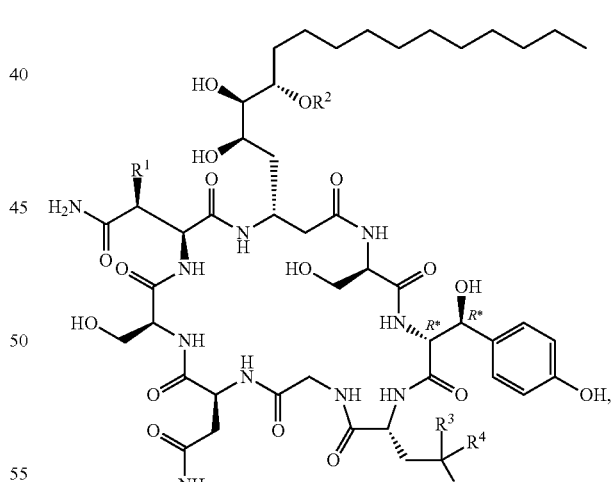

wherein R[1] is hydrogen or hydroxyl; wherein R[2] is hydrogen or xylose; and wherein R[3] and R[4] are each hydrogen or together oxygen, thereby treating or preventing of fungal infection in the plant.

Also disclosed are methods for inhibiting fungal growth on a surface, comprising applying to the surface an effective amount of a compound, or a salt thereof, having a structure represented by a formula:

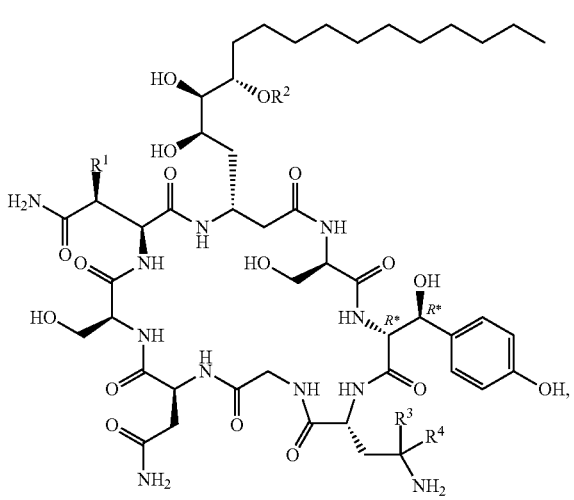

wherein $R^1$ is hydrogen or hydroxyl; wherein $R^2$ is hydrogen or xylose; and wherein $R^3$ and $R^4$ are each hydrogen or together oxygen.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

Figure 1:
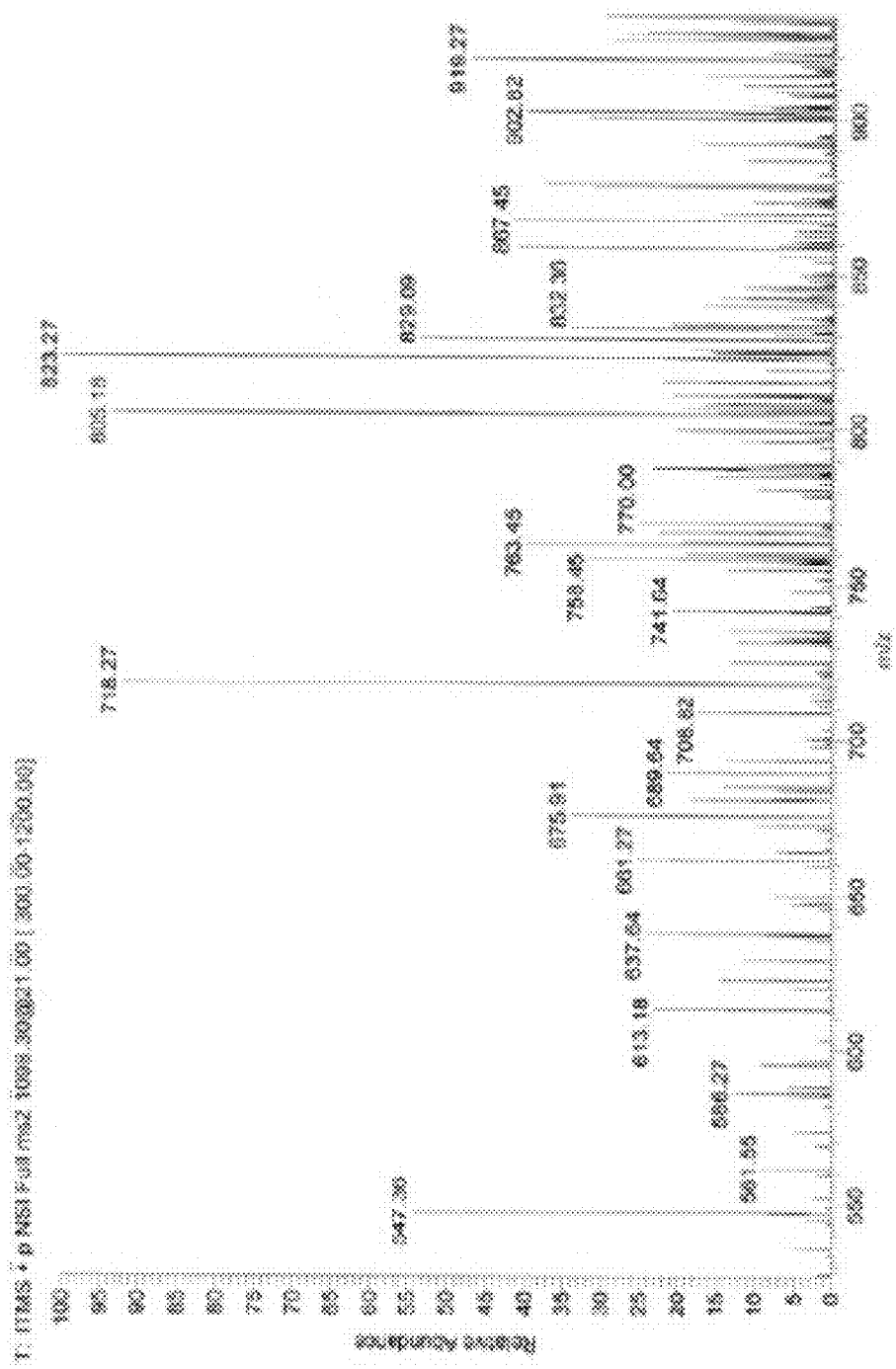
FIG. 1 shows the Ion Trap MS (ITMS) spectrum of 2: Bk-1097.
Figure 1:
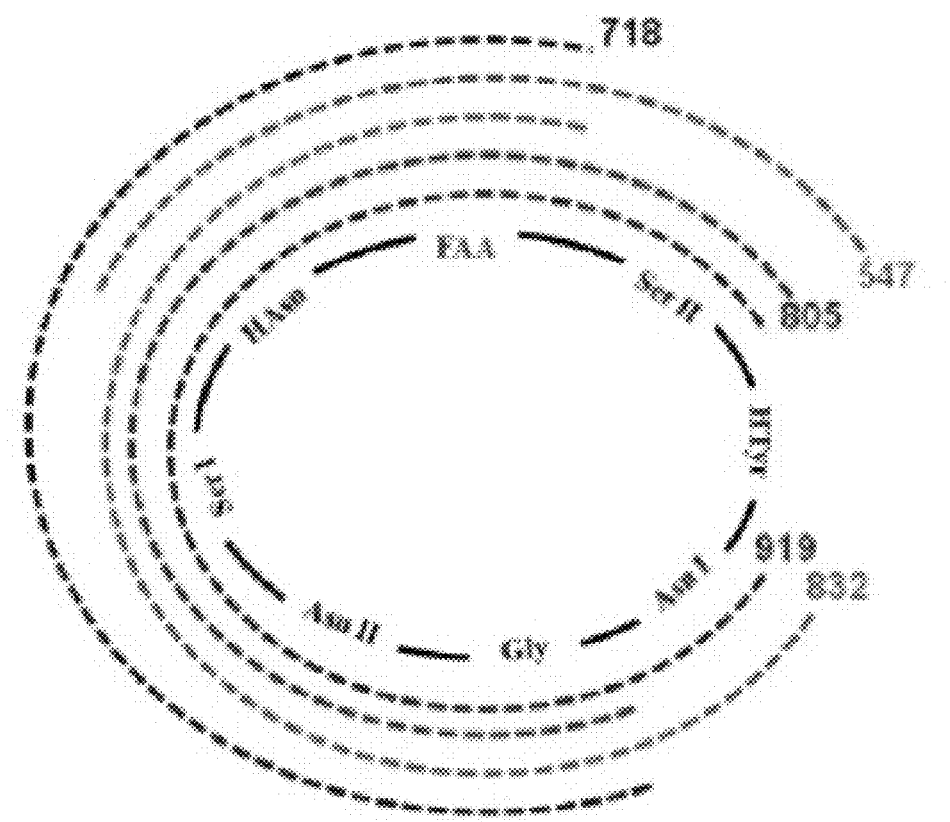
Figure 2:
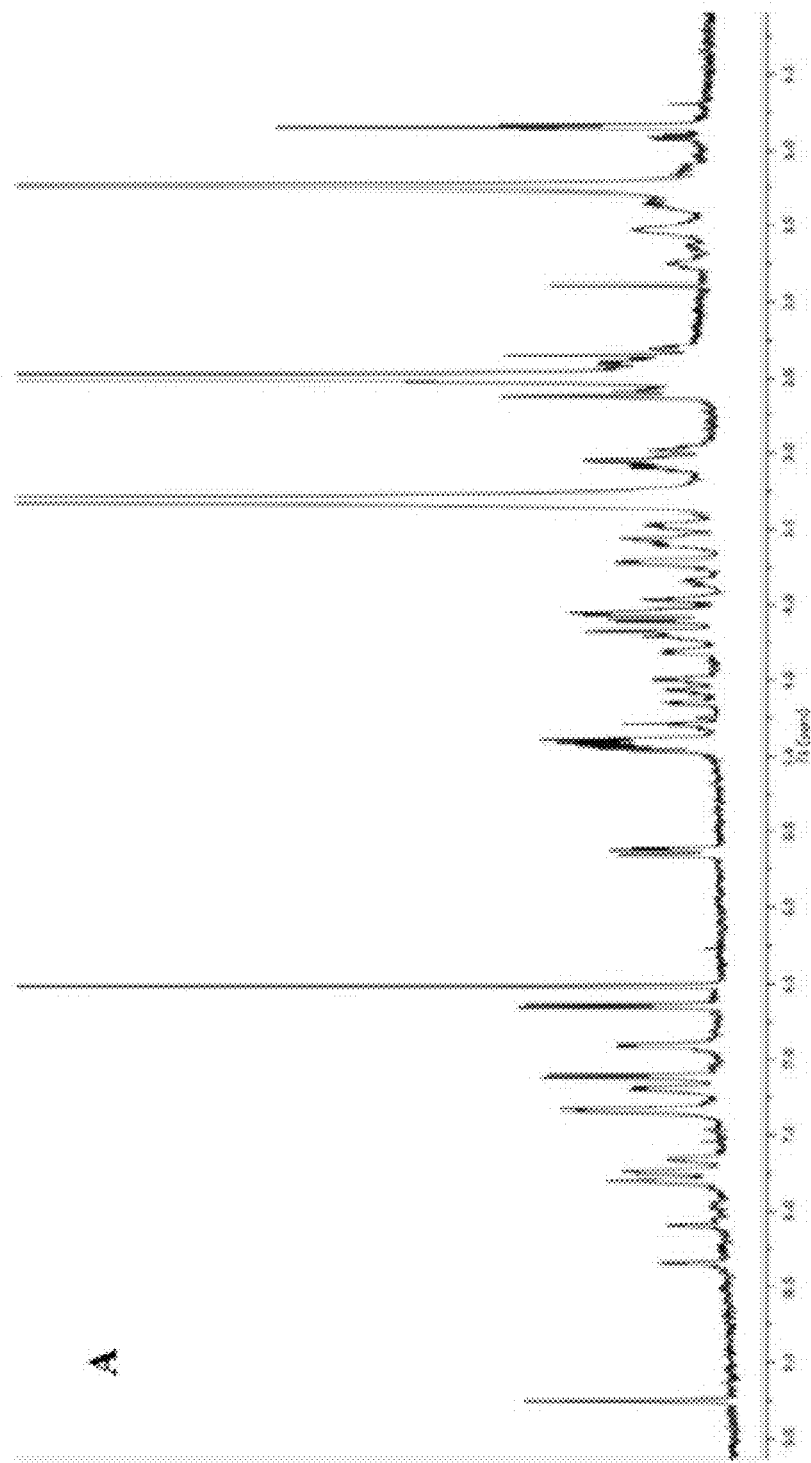
FIG. 2 shows the $^1$H NMR spectrum in DMSO-$d_6$. A: Bk-1229, B: Bk-1097.
Figure 2:
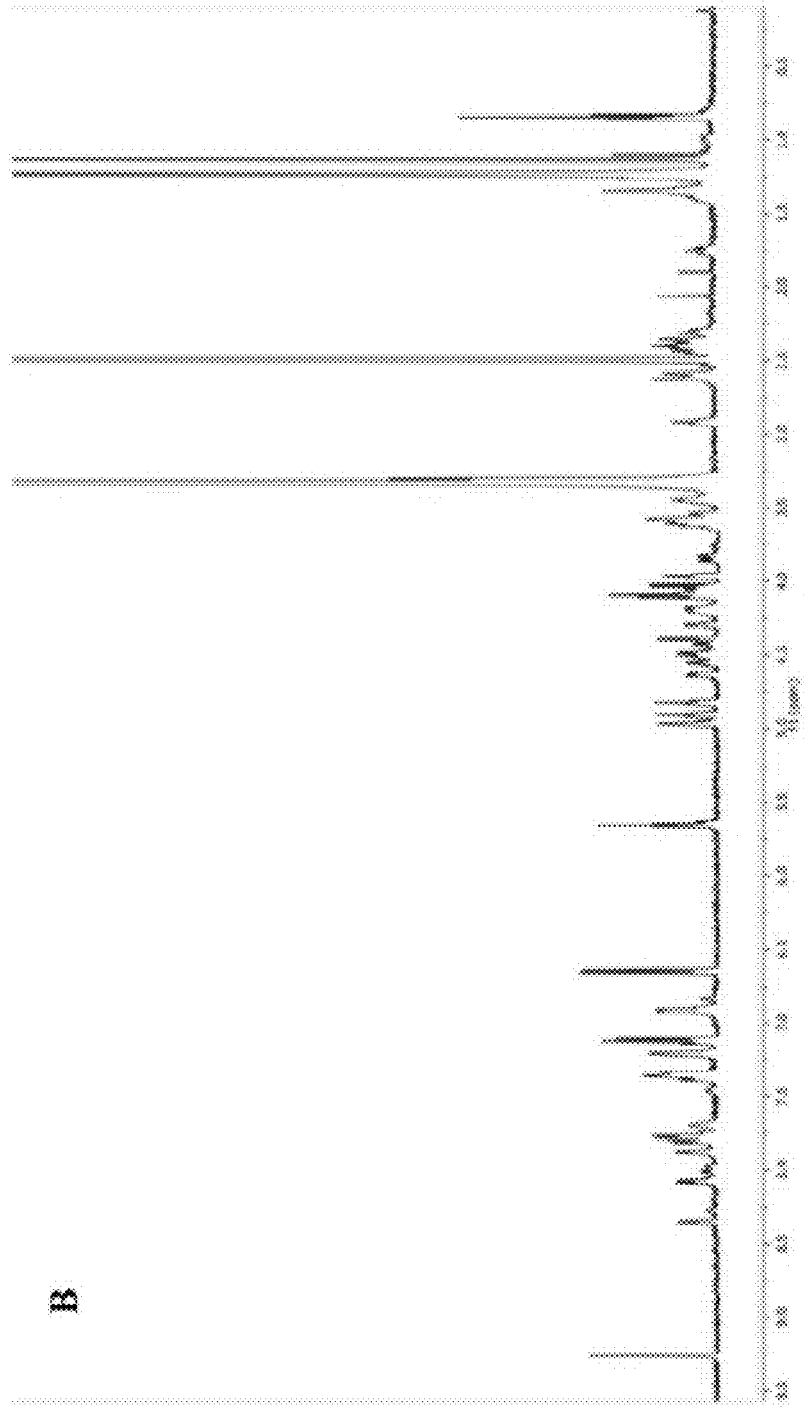
Figure 3:
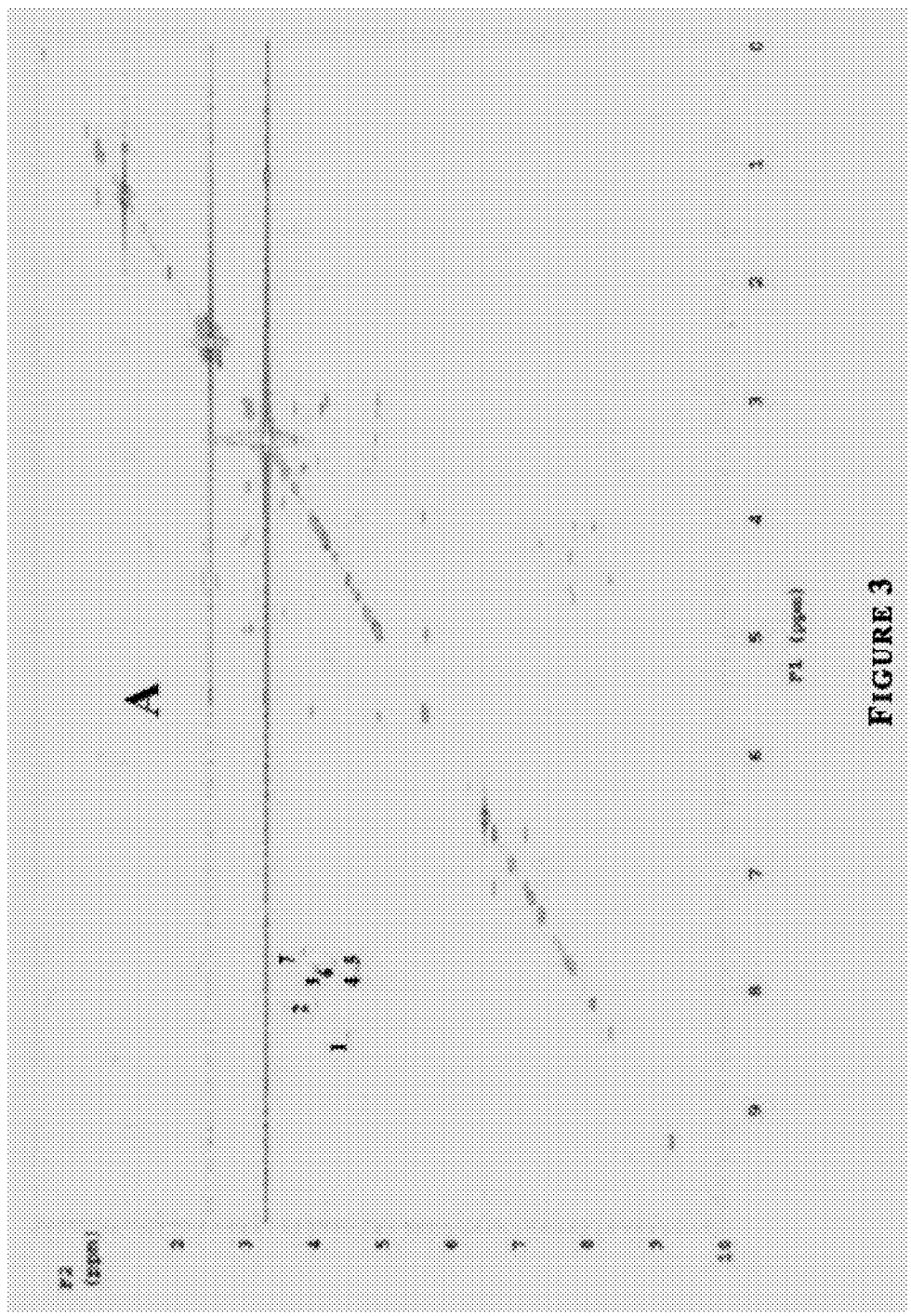
FIG. 3 shows the COSY spectrum in DMSO-$d_6$. A: Bk-1229 full spectrum, B: Bk-1229 expanded region, and Bk-1097 full spectrum. Numbers show COSY correlations between amide and α-protons.
Figure 3:
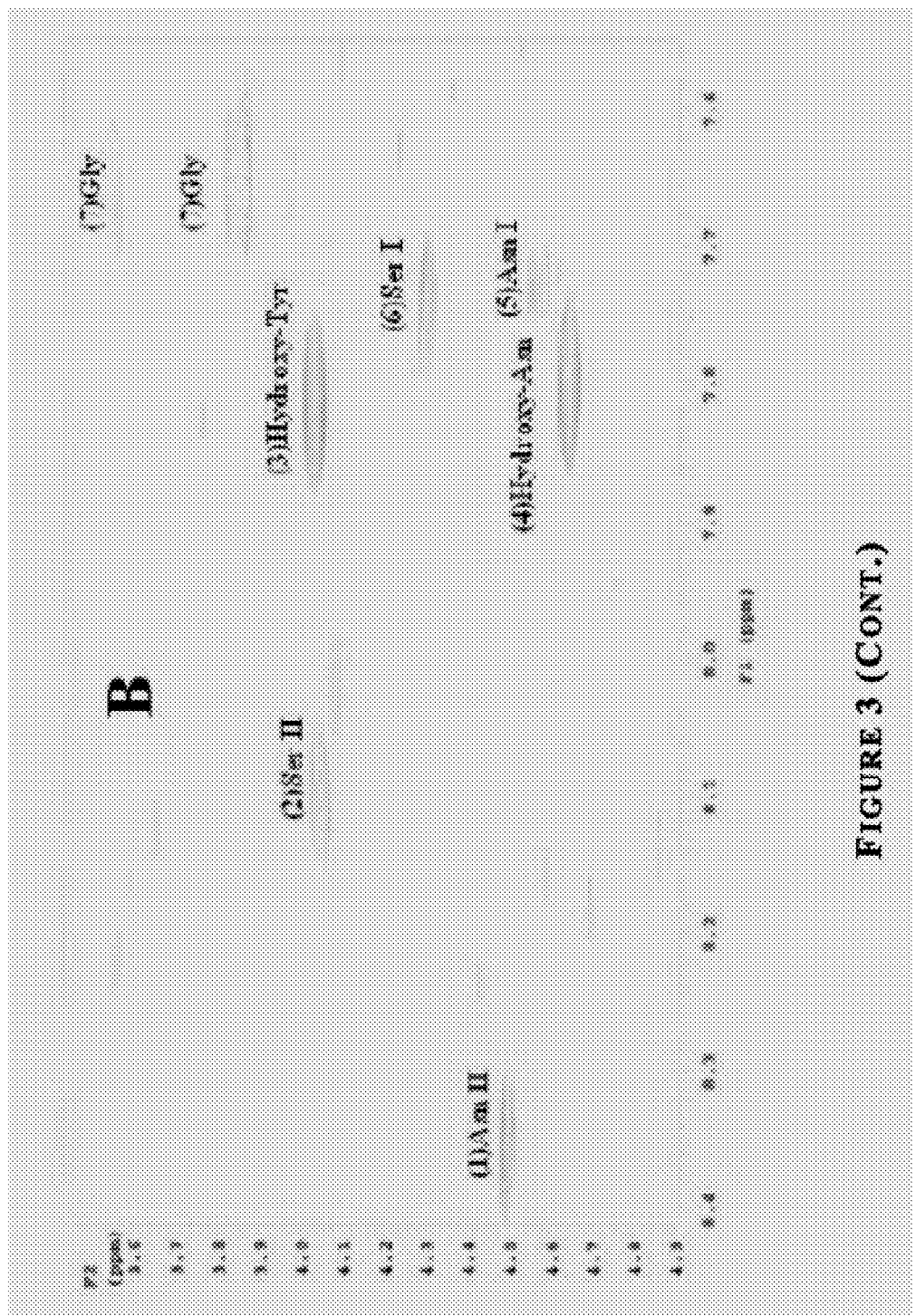
Figure 3:
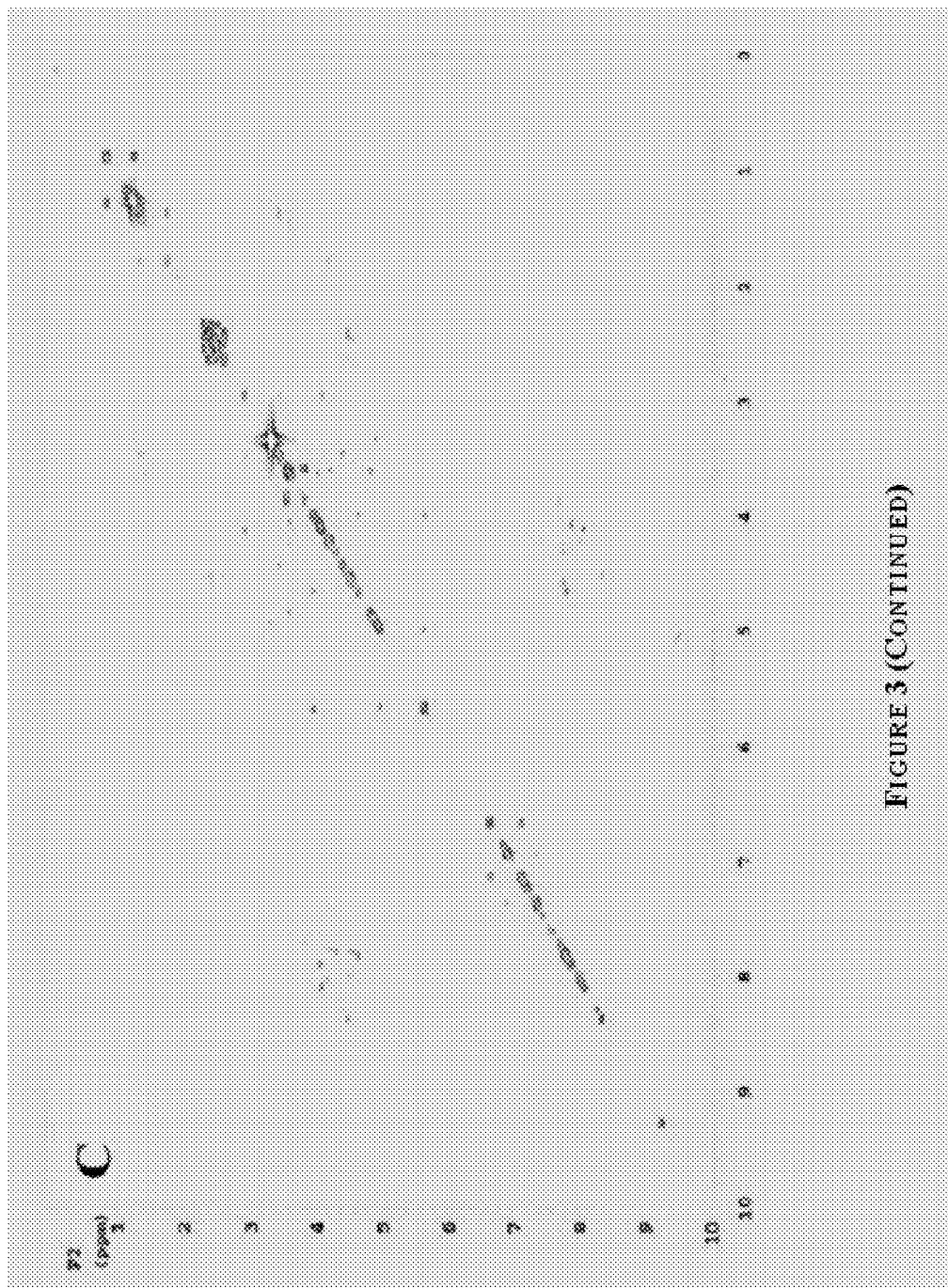
Figure 4:
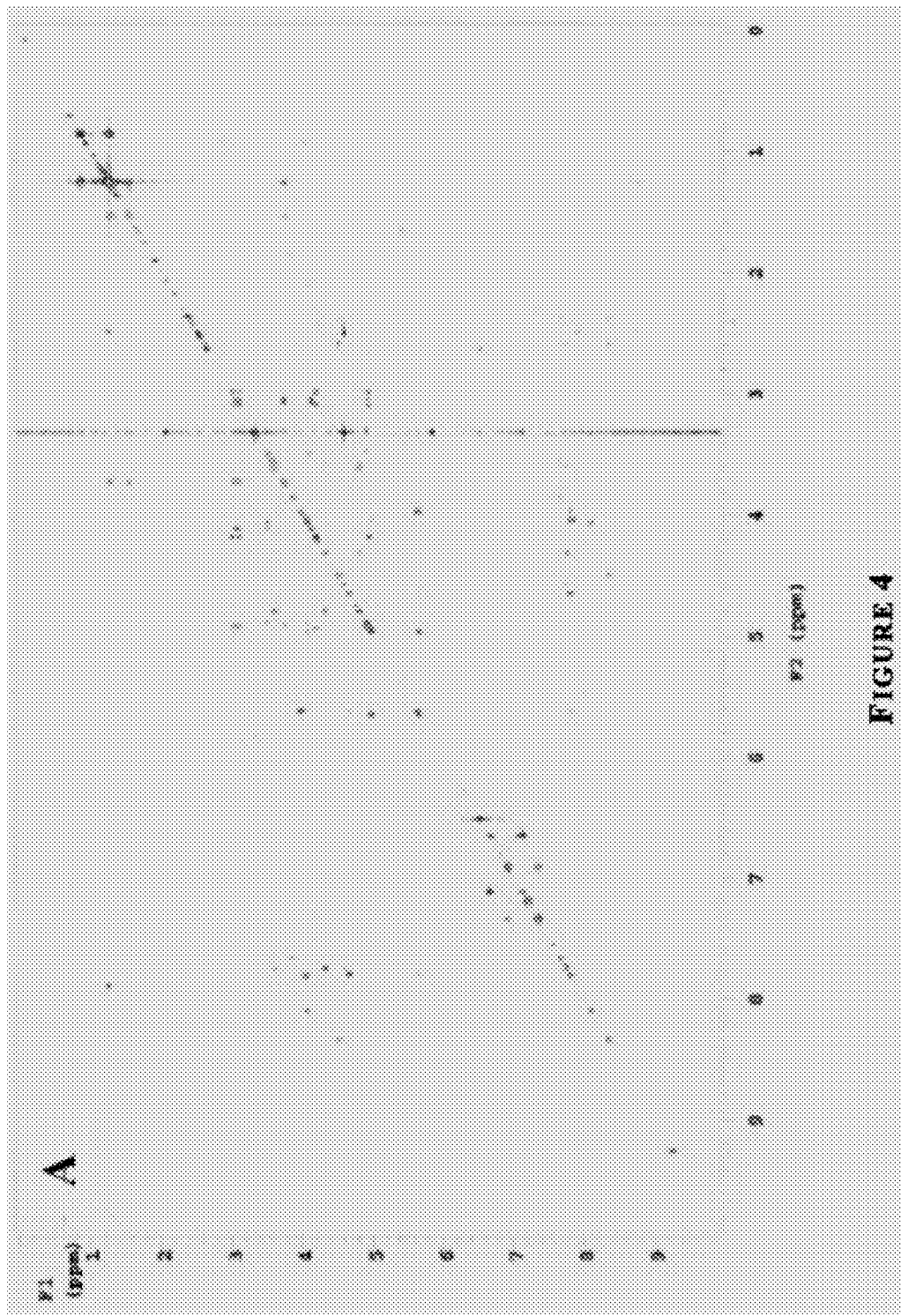
FIG. 4 shows a graph the TOCSY spectrum in DMSO-$d_6$. A: Bk-1229 full spectrum, B: Bk-1229 expanded region, and Bk-1097 full spectrum.
Figure 4:
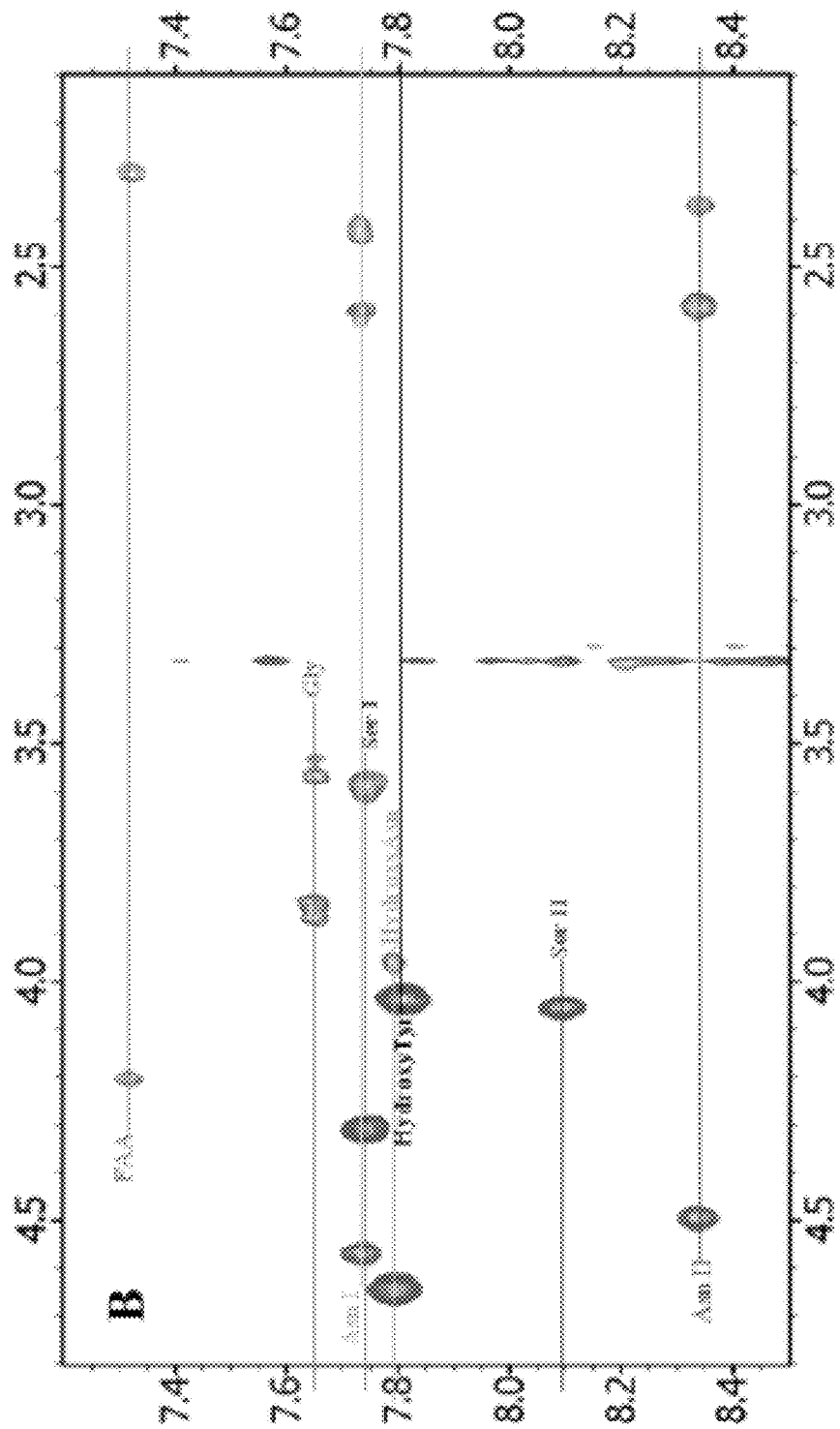
Figure 4:
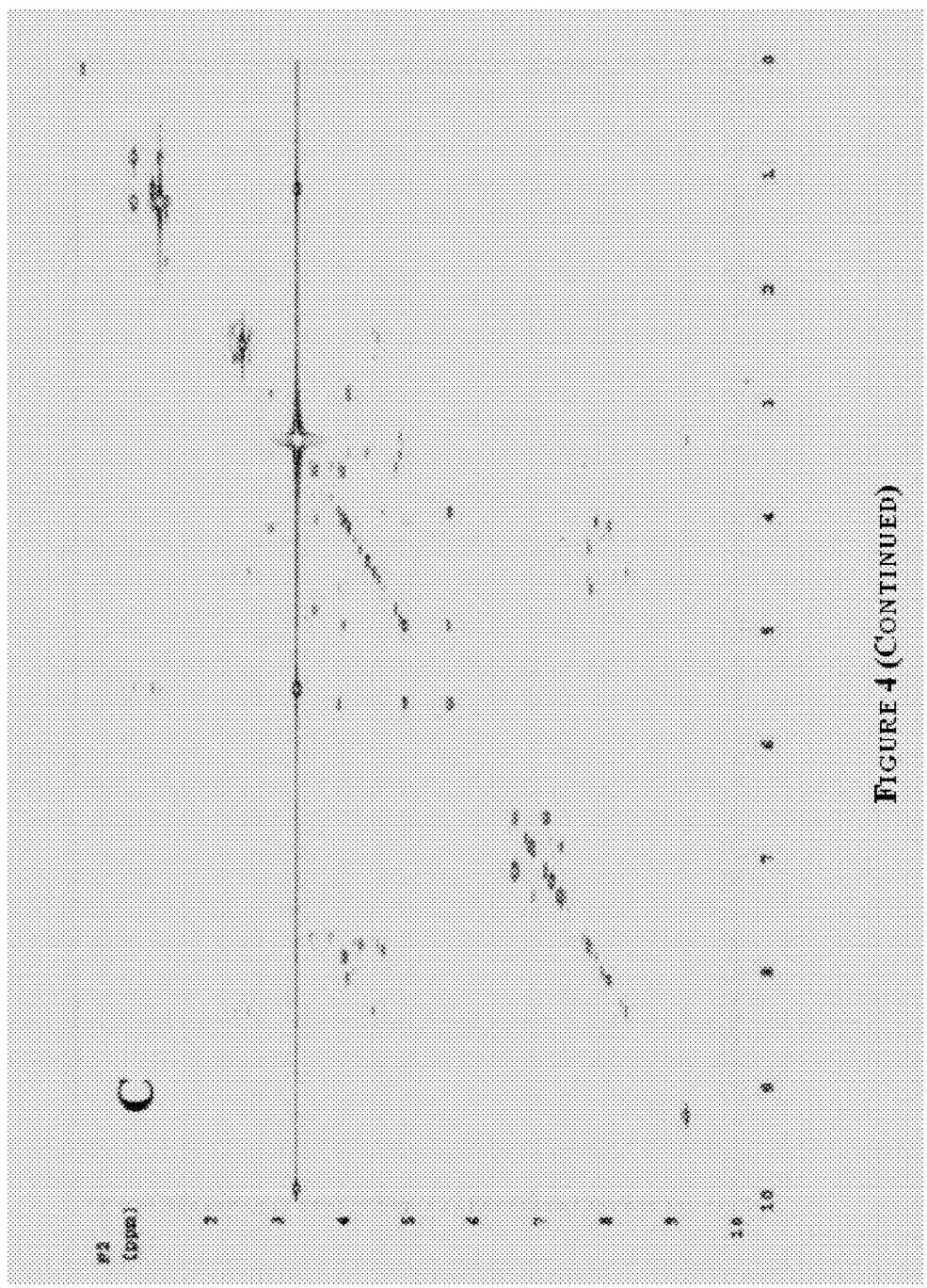
Figure 5:
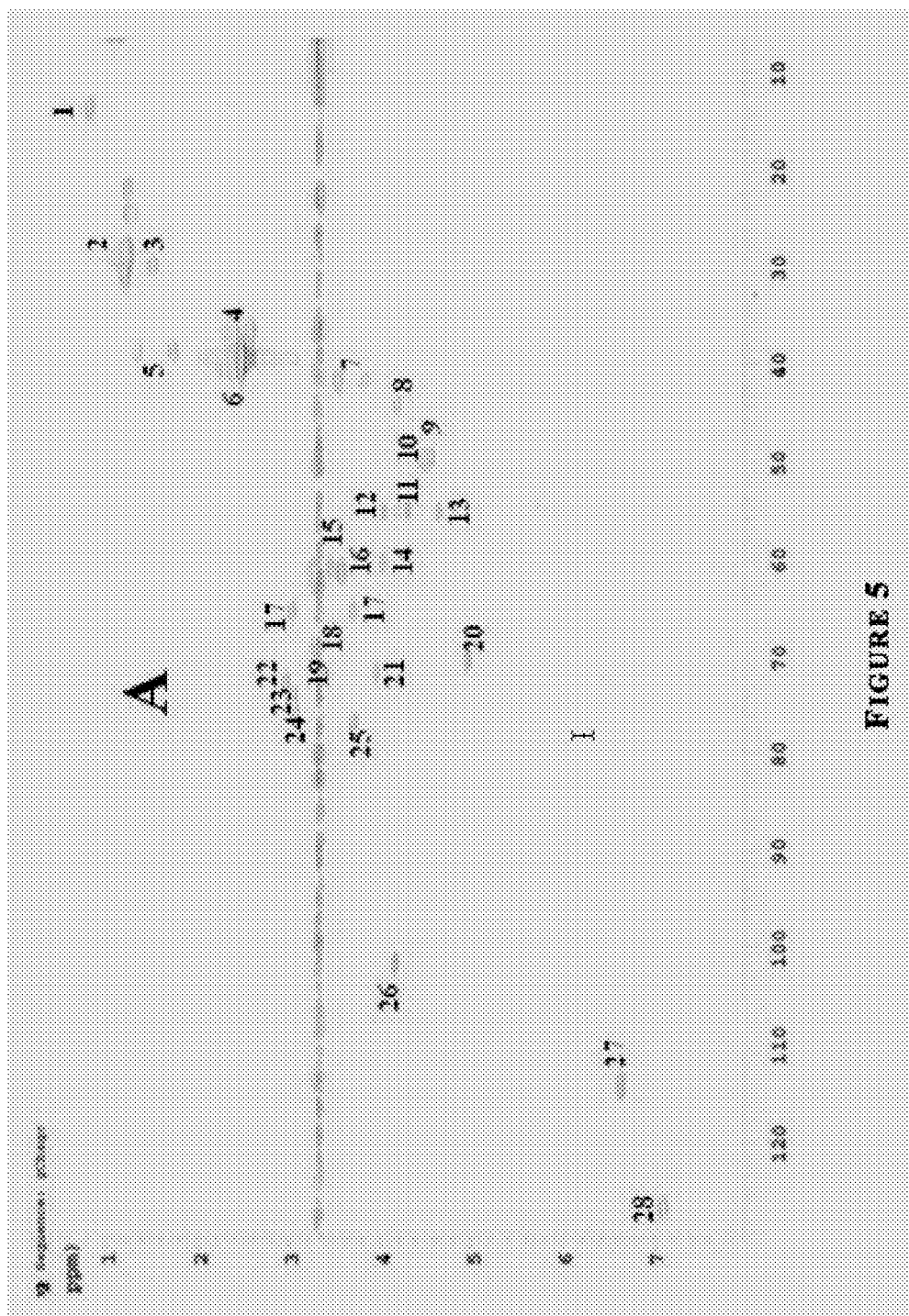
FIG. 5 shows a graph that shows the HSQC spectrum in DMSO-$d_6$. A: Bk-1229 full spectrum, and B: Bk-1229 expanded region.
Figure 5:
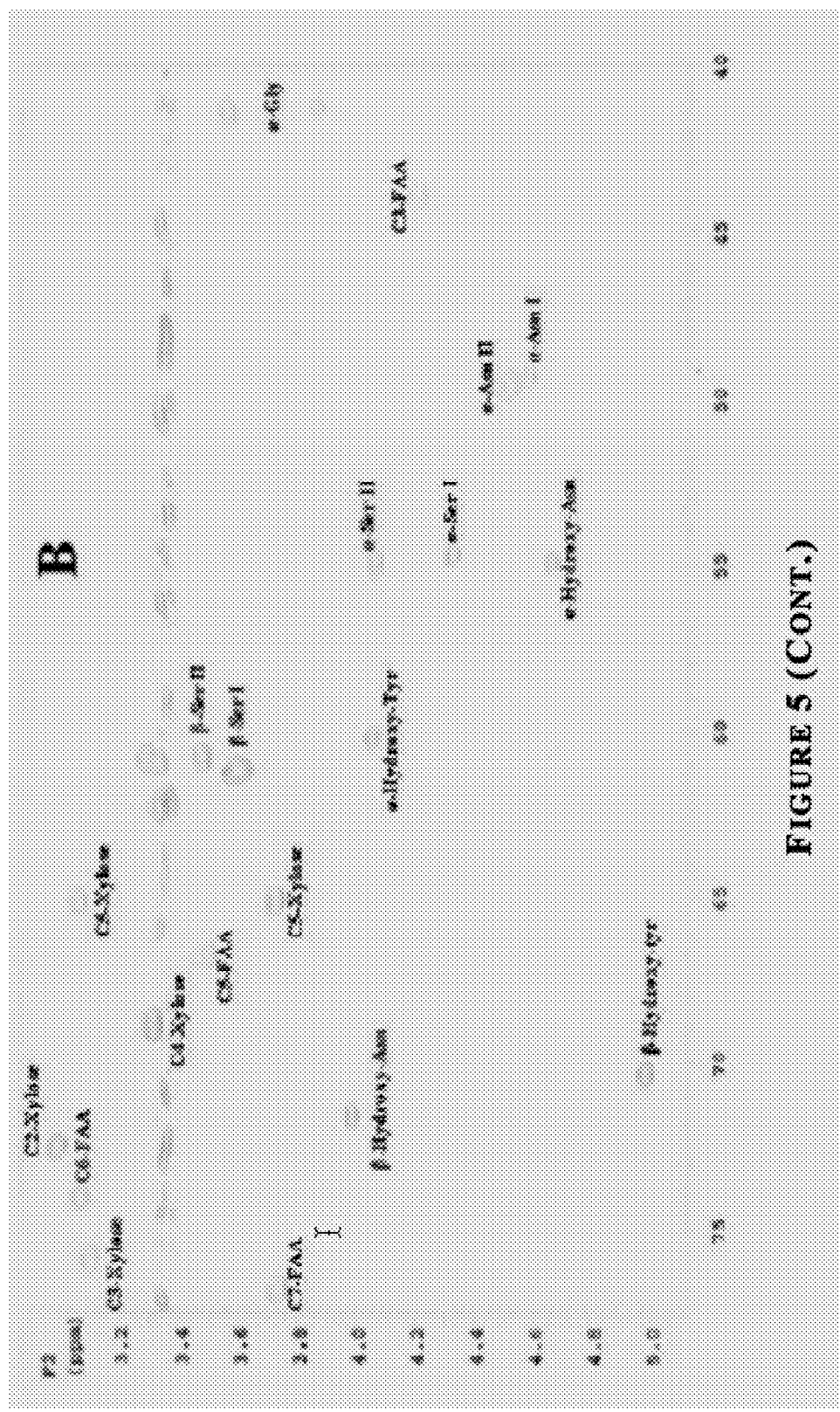
Figure 5:
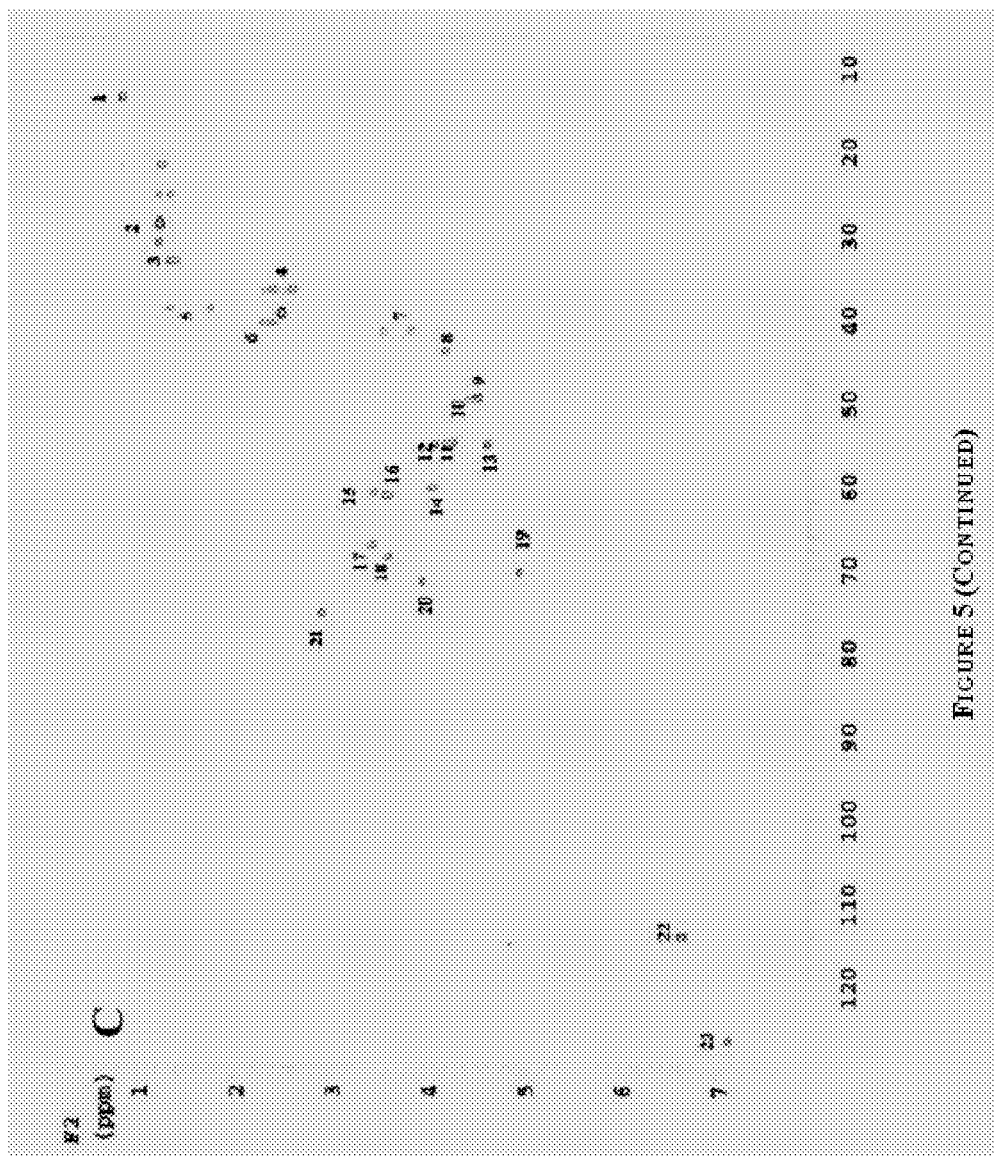
Figure 6:
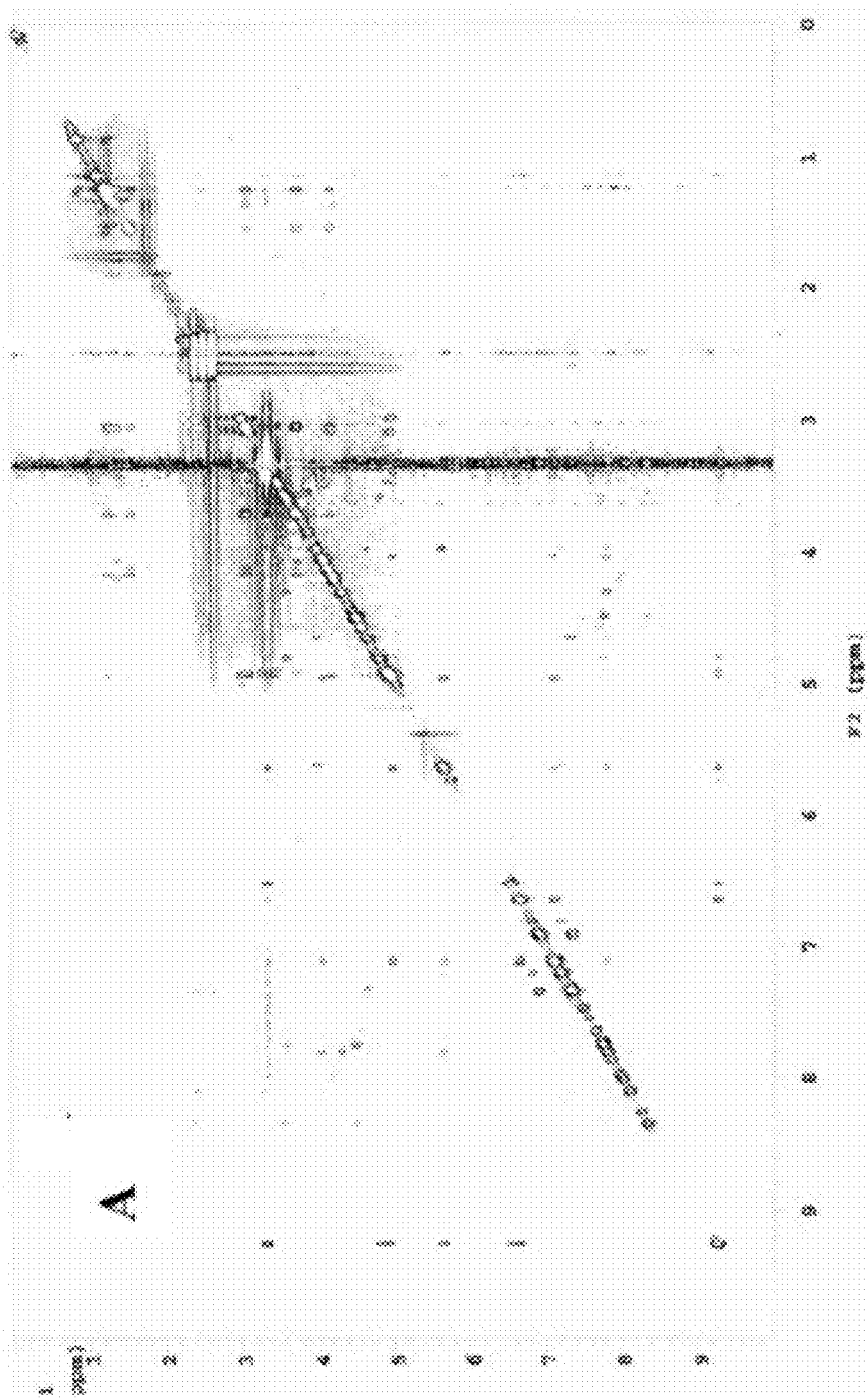
FIG. 6 shows a graph that shows the ROESY spectrum in DMSO-$d_6$. A: Bk-1229 full spectrum, B: Bk-1229 expanded (fingerprint) region, the assignment of crosspeaks in FIG. 6(B), and C: Bk-1097 full spectrum.
Figure 6:
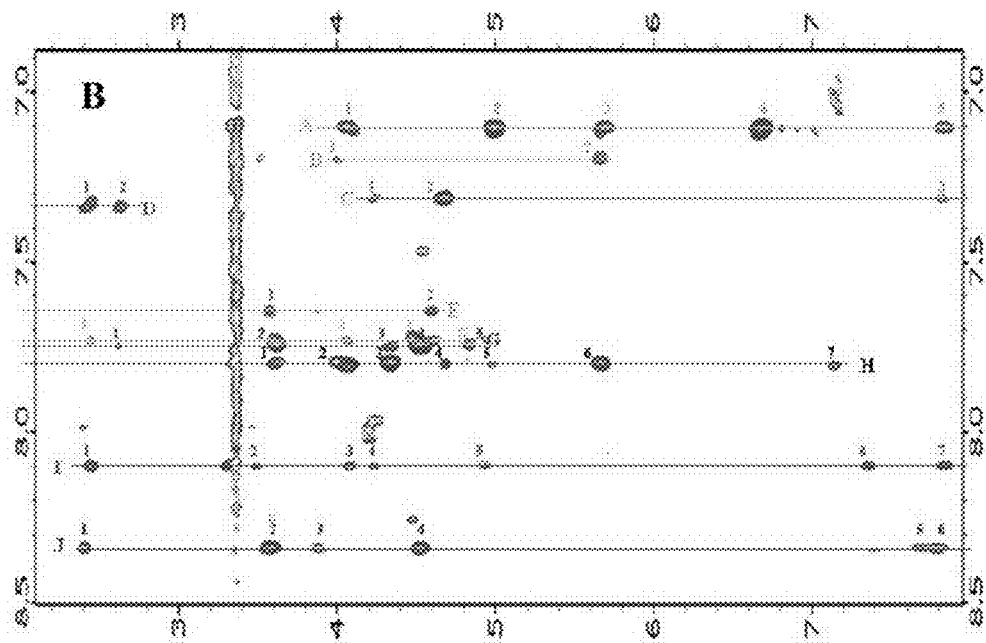
Figure 6:
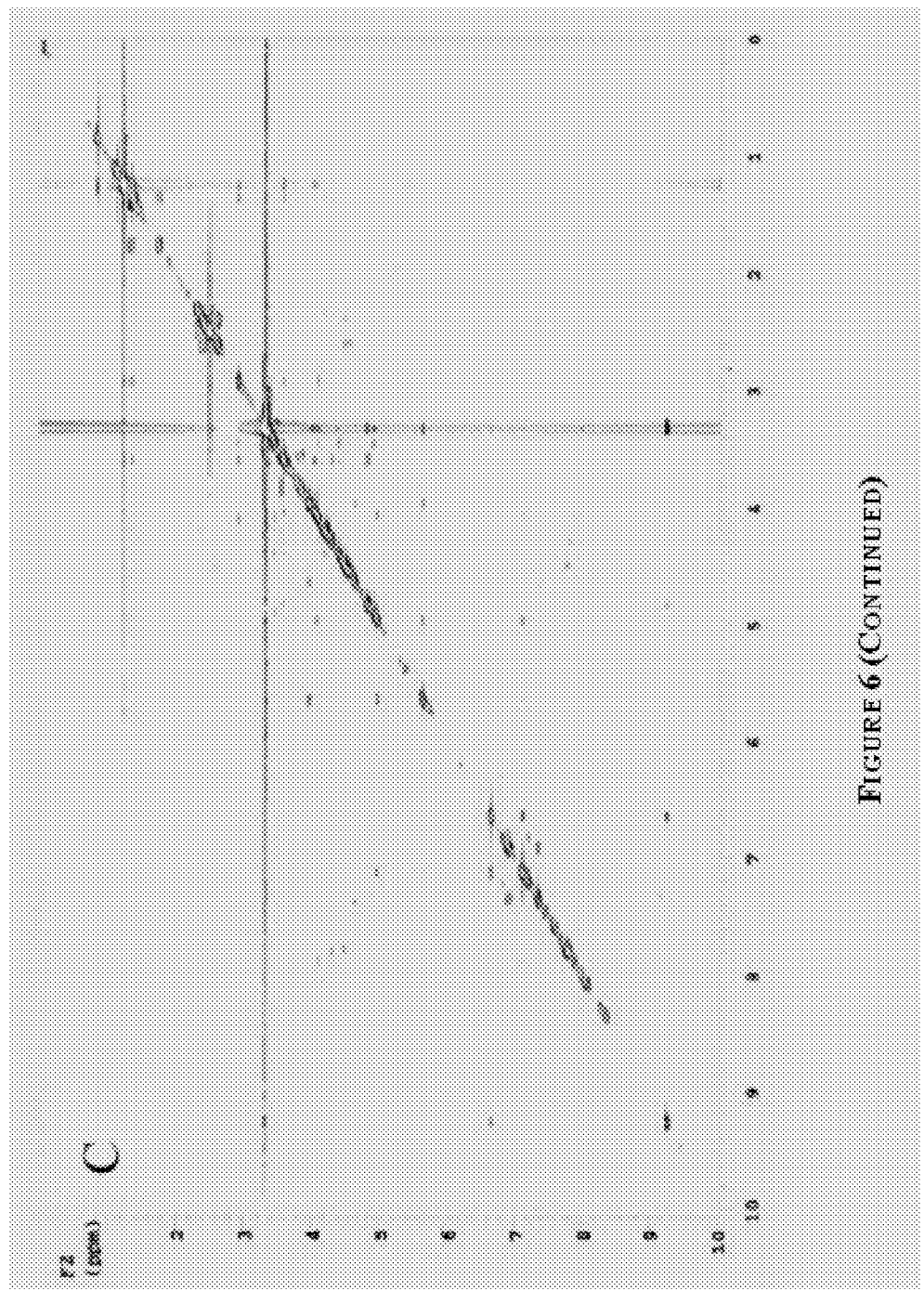
Figure 7:
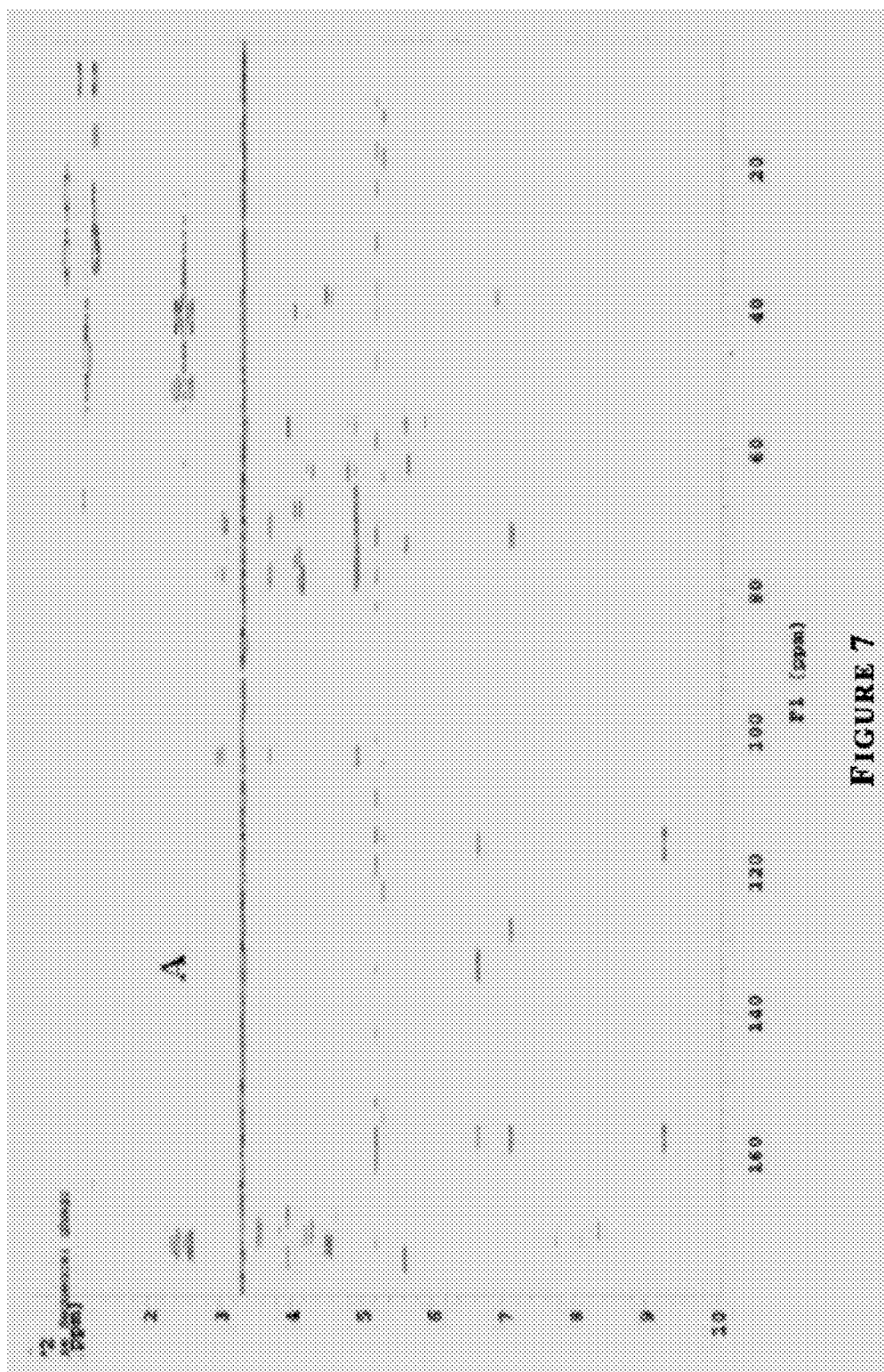
FIG. 7 shows the HMBC spectrum in DMSO-$d_6$. A: Bk-1229, and B: Bk-1097.
Figure 7:
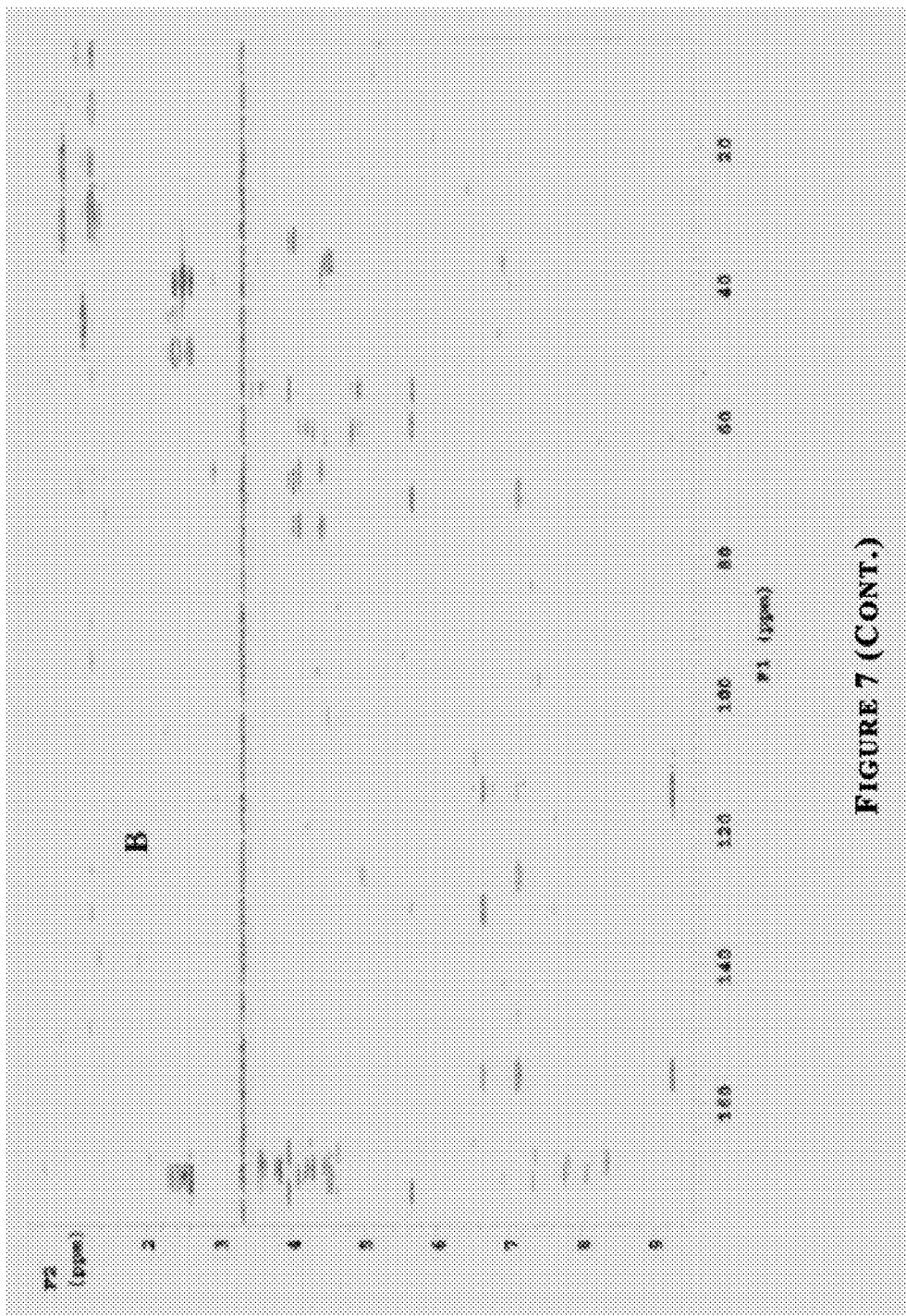
Figure 8:
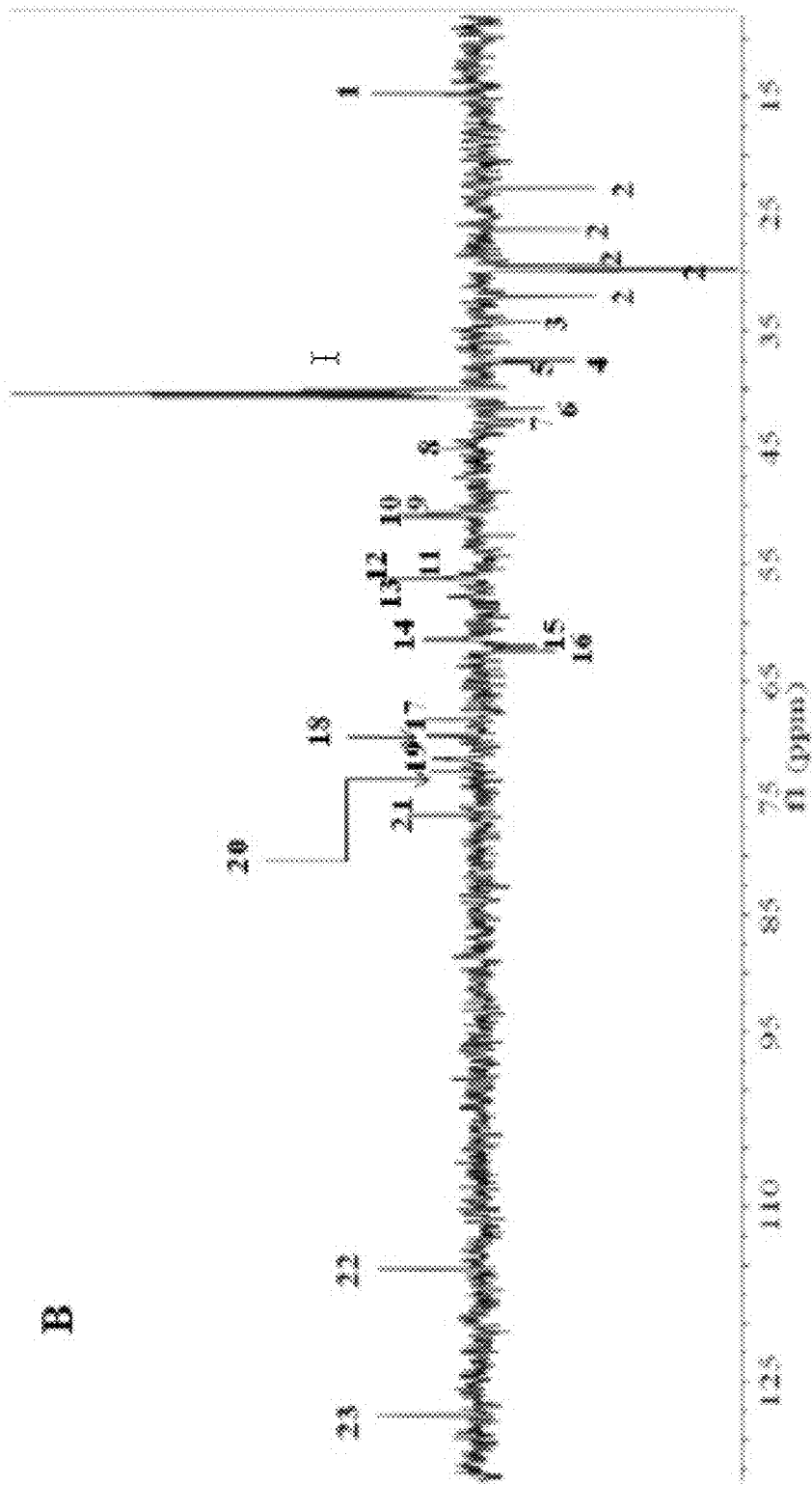
FIG. 8 shows the $^{13}$C spectrum of 2 in DMSO-$d_6$, and the DEPT spectrum of 2 in DMSO-$d_6$. Numbers show the order of carbons as in Table 1.
Figure 9:
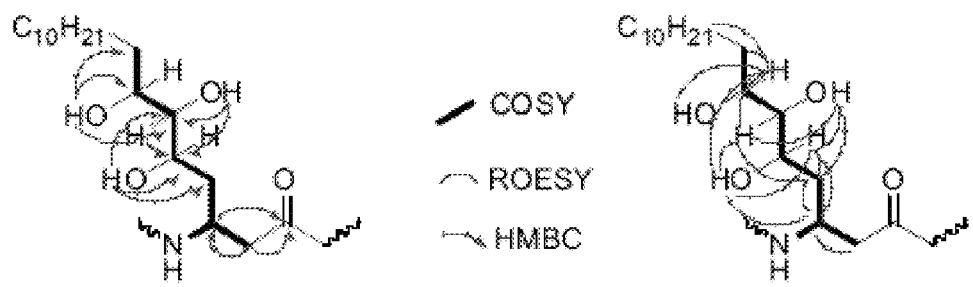
FIG. 9 shows the structure of fatty acyl amino acid (FAA) of 2 showing COSY, HMBC and ROESY correlations.
Figure 10:
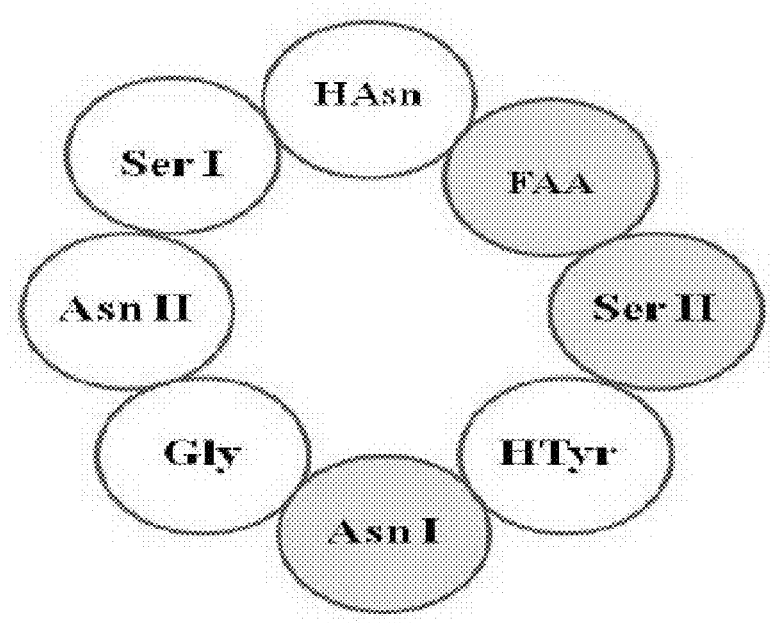
FIG. 10 shows representative structure of Bk-1229.
Figure 11:
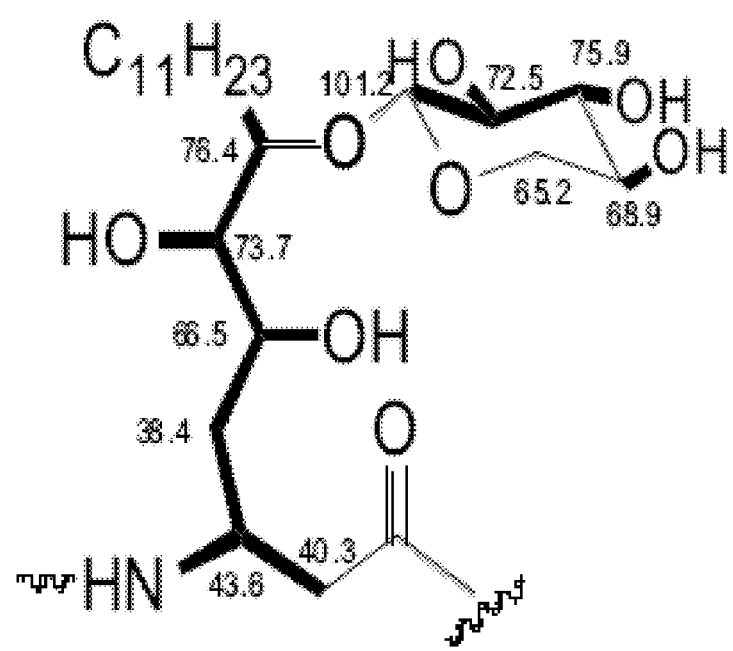
FIG. 11 shows the structure of fatty acyl amino acid (FAA) of Bk-1229.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such component, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "optional" or "optionally" means that the subsequently described event or circumstance may or may not occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment prior to the administering step. In some aspects of the disclosed methods, the subject has been identified to be in need of treatment for a disorder, which refers to selection of a subject based upon need for treatment of the disorder. It is contemplated that the identification can, in one aspect, be performed by a person different from the person making the diagnosis. It is also contemplated, in a further aspect, that the administration can be performed by one who subsequently performed the administration.

As used herein, the term "plant" can be, but is not limited to, a cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fiber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) or plants such as tobacco, nuts, coffee, eggplants, sugarcane, tea, pepper, vines including grape-bearing vines, hops, bananas, turf and natural rubber plants, as well as ornamentals (flowers, shrubs, broad-leafed trees, evergreens, geraniums, azaleas, roses, tulips, petunias, orchids, carnations, poinsettias, chrysanthemums; and conifers such as pine, yew, spruce).

As used herein, the terms "Bk-1229" and "burkholdine 1229" refer to an isolated compound having a structure represented by a formula:

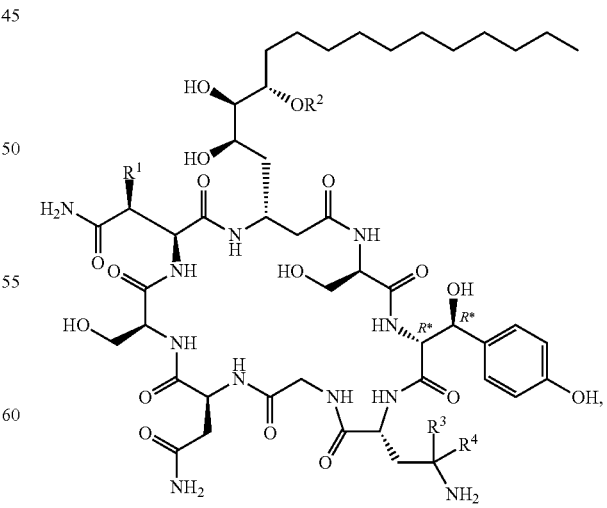

wherein $R^1$ is hydroxyl; wherein $R^2$ is xylose; and wherein $R^3$ and $R^4$ are together oxygen.

As used herein, the terms "Bk-1097" or "burkholdine 1097" refer to an isolated compound having a structure represented by a formula:

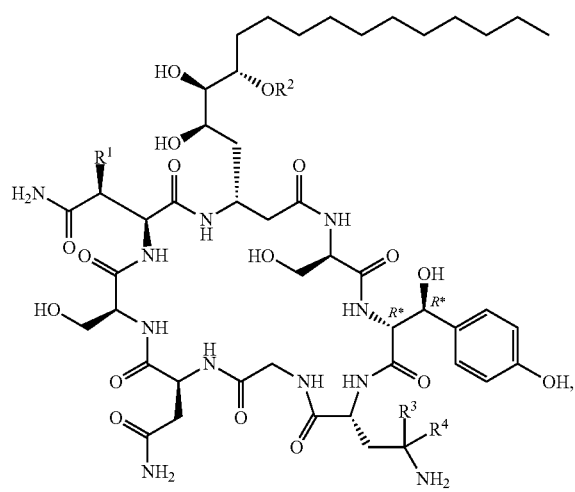

wherein $R^1$ is hydroxyl; wherein $R^2$ is hydrogen; and wherein $R^3$ and $R^4$ are together oxygen.

As used herein, the term "inhibiting" refers to the adverse effects against a microorganism, such as retarding, suppressing or stopping growth of the microorganism or killing or lysing the microorganism. The adverse effect on growth may be temporary or permanent.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a fungal infection" means having been subjected to a physical examination by a person of skill, for example, a physician, and found to have a condition that can be diagnosed or treated by a compound or composition that anti-fungal or fungicidal activity. As a further example, "diagnosed with a need for anti-fungal treatment" refers to having been subjected to a physical examination by a person of skill, for example, a physician, and found to have a condition characterized by a fungal infection. Such a diagnosis can be in reference to a disorder, such as a neurodegenerative disease, and the like, as discussed herein.

As used herein, the phrase "identified to be in need of treatment for a disorder," or the like, refers to selection of a subject based upon need for treatment of the disorder. For example, a subject can be identified as having a need for treatment of a disorder (e.g., a fungal infection) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, sublingual administration, buccal administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side affects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an Internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$IC_{50}$," is intended to refer to the concentration of a substance (e.g., a compound or a drug) that is required for 50% inhibition of a biological process, or component of a process, including a fungus, protein, subunit, etc. For example, $IC_{50}$ refers to the half maximal (50%) inhibitory concentration (IC) of a substance as determined in a suitable assay.

The term "pharmaceutically acceptable" describes a material that is not biologically or otherwise undesirable, i.e., without causing an unacceptable level of undesirable biological effects or interacting in a deleterious manner.

The term "agriculturally acceptable" describes a material that is not undesirable for use with crops, i.e., without causing an unacceptable level of undesirable effects or interacting in a deleterious manner.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "hydroxyl" as used herein is represented by the formula —OH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture.

Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

B. COMPOUNDS

In one aspect, the invention relates to an isolated compound having a structure represented by a formula:

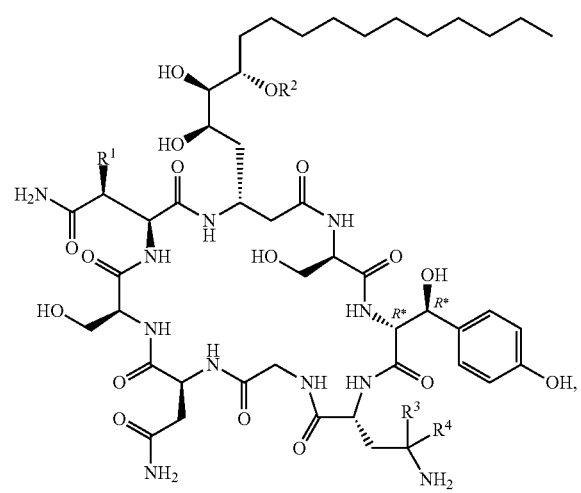

wherein $R^1$ is hydrogen or hydroxyl; wherein $R^2$ is hydrogen or xylose; and wherein $R^3$ and $R^4$ are each hydrogen or together oxygen.

In one aspect, $R^3$ and $R^4$ are each hydrogen. In a further aspect, $R^1$ is hydrogen. In a still further aspect, $R^1$ is hydroxyl. In yet a further aspect, $R^2$ is hydrogen. In yet a further aspect $R^2$ has a structure represented by a formula:

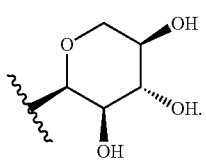 [SMILES: *[C@H]1OC[C@@H](O)[C@H](O)[C@H]1O]

In yet a further aspect, $R^2$ has a structure represented by a formula:

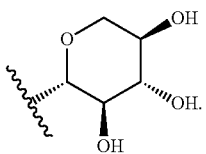 [SMILES: *[C@@H]1OC[C@@H](O)[C@H](O)[C@H]1O]

In one aspect, $R^3$ and $R^4$ are together oxygen. In a further aspect, $R^1$ is hydrogen. In a still further aspect, $R^1$ is hydroxyl. In a yet further aspect, $R^2$ is hydrogen. In yet a further aspect, $R^2$ has a structure represented by a formula:

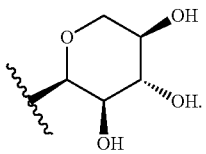 [SMILES: *[C@H]1OC[C@@H](O)[C@H](O)[C@H]1O]

In yet a further aspect, $R^2$ has a structure represented by a formula:

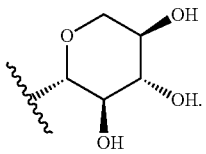 [SMILES: *[C@@H]1OC[C@@H](O)[C@H](O)[C@H]1O]

In one aspect, the invention relates to an isolated compound having a structure represented by a formula:

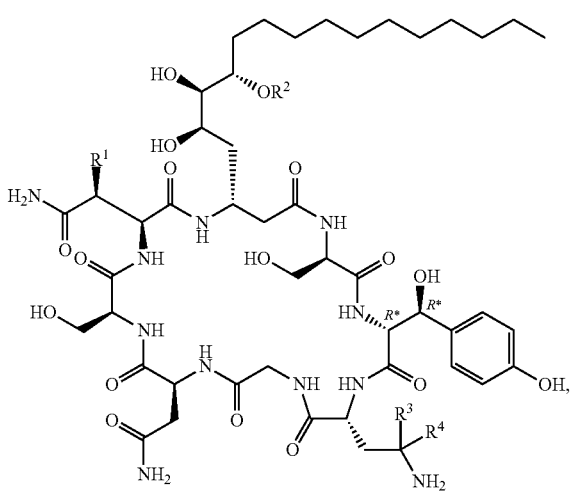

wherein $R^1$ is hydrogen or hydroxyl; wherein $R^2$ is hydrogen or xylose; and wherein $R^3$ and $R^4$ are each hydrogen or together oxygen. In a further aspect, the compound is present in at least about 50% purity. In a still further aspect, the compound is present in at least about 75% purity. In a yet further aspect, the compound is present in at least about 90% purity. In a yet further aspect, the compound is present in at least about 95% purity. In yet a further aspect, the compound is present in at least about 99% purity.

In one aspect, the compound is isolated from beta-proteobacteria. In a further aspect, the compound is isolated from *Burkholderia* or *Pseudomonas* species. In a still further aspect, the compound is isolated from *Burkholderia* species. In a yet further aspect, the compound is isolated from *Burkholderia ambifaria*. In yet a further aspect, the compound is isolated from *Burkholderia ambifaria* strain 2.2 N.

C. ANTI-FUNGAL ACTIVITY

The utility of the compounds in accordance with the present invention as inhibitors of fungal cell growth, can be demonstrated by methodology known in the art.

In one aspect, the compound exhibits antifungal activity against *Botrytis, Mycosphaerella, Cercospora, Rhizoctonia, Monilinia, Phytophthora, Alternaria, Candida, Saccharomyces, Aspergillus, Pseudocercosporella, Cladosporium, Chaetomium, Fusarium, Colletotrichum, Epidermophyton, Trichophyton,* or *Microsporum*.

In one aspect, the compound is cytotoxic. In a further aspect, the compound inhibits fungal cell growth compound with a MIC of less than about 12.5 µg/ml. In a still further aspect, the compound inhibits fungal cell growth compound with a MIC of less than about 1.6 µg/ml. In a yet further aspect, the compound inhibits fungal cell growth compound with a MIC of less than about 0.4 µg/ml.

In one aspect, the compound exhibits of about at least 50% fungal cell growth inhibition with an IC of less than about 2000 ppm. In a further aspect, the compound exhibits of about at least 50% fungal cell growth inhibition with an IC of less than about 1000 ppm. In a still further aspect, the compound exhibits of about at least 50% fungal cell growth inhibition with an IC of less than about 500 ppm. In a yet further aspect, the compound exhibits of about at least 50% fungal cell growth inhibition with an IC of less than about 100 ppm. In yet a further aspect, the compound exhibits of about at least 50% fungal cell growth inhibition with an IC of less than about 20 ppm.

In one aspect, the compound exhibits of about at least 75% fungal cell growth inhibition with an IC of less than about 2000 ppm. In a further aspect, the compound exhibits of about at least 75% fungal cell growth inhibition with an IC of less than about 1000 ppm. In a still further aspect, the compound exhibits of about at least 75% fungal cell growth inhibition with an IC of less than about 500 ppm. In a yet further aspect, the compound exhibits of about at least 75% fungal cell growth inhibition with an IC of less than about 100 ppm. In yet a further aspect, the compound exhibits of about at least 75% fungal cell growth inhibition with an IC of less than about 20 ppm.

In one aspect, the compound exhibits of about at least 90% fungal cell growth inhibition with an IC of less than about 2000 ppm. In a further aspect, the compound exhibits of about at least 90% fungal cell growth inhibition with an IC of less than about 1000 ppm. In a still further aspect, the compound exhibits of about at least 90% fungal cell growth inhibition with an IC of less than about 500 ppm. In a yet further aspect, the compound exhibits of about at least 90% fungal cell growth inhibition with an IC of less than about 100 ppm. In yet a further aspect, the compound exhibits of about at least 90% fungal cell growth inhibition with an IC of less than about 20 ppm.

D. METHODS OF PROVIDING THE COMPOUNDS

In one aspect, the invention relates to methods of producing the disclosed compounds useful as fungal growth inhibitors, which can be useful in the treatment or prevention of fungal infections and other conditions in which inhibition or killing of fungal cells is desired.

The compounds of this invention can be prepared by employing cell culturing, extraction, and isolation methods as shown in the following section, in addition to other standard manipulations that are known in the literature, exemplified in the experimental sections or clear to one skilled in the art.

Methods used to isolate the compounds of this invention are prepared by employing methods as shown in the following section, in addition to other standard isolation methods known in the literature or to one skilled in the art. The following examples are provided so that the invention might be more fully understood, are illustrative only, and should not be construed as limiting.

In a one aspect, a compound comprises the product of the disclosed methods. In a still further aspect, the invention comprises a pharmaceutical composition comprising a therapeutically effective amount of the product of the disclosed methods and a pharmaceutically acceptable carrier. In a further aspect, the invention comprises a agricultural composition comprising a therapeutically effective amount of the product of the disclosed methods and an agriculturally acceptable carrier. In a still further aspect, the invention comprises a method for manufacturing a medicament comprising combining at least one compound of any of disclosed compounds or at least one product of the disclosed methods with a pharmaceutically acceptable carrier or diluent.

In one aspect, the invention relates to a method of isolating the disclosed compounds comprising the steps of providing a fermentation broth of bacterial cultures of *Burkholderia ambifaria* and extracting the compound from the fermentation broth. In a further aspect, the method further comprises spray-drying or freeze-drying the fermentation broth. In a still further aspect, the method further comprises purifying the compound by solvent-liquid extraction. In a still further aspect, the method further comprises purifying the compound by solid-liquid extraction. In a still further aspect, the method further comprises purifying the compound by revered phase high pressure liquid chromatography.

In one aspect, the method further comprises heat-treating the fermentation broth to a temperature sufficient to kill the bacteria. In a further aspect, the method further comprises comprising heating the fermentation broth to at least about 80° C.

In one aspect, the compound is isolated from beta-proteobacteria. In a further aspect, the compound is isolated from *Burkholderia* or *Pseudomonas* species. In a still further aspect, the compound is isolated from *Burkholderia* species. In a yet further aspect, the compound is isolated from *Burkholderia ambifaria*. In yet a further aspect, the compound is isolated from *Burkholderia ambifaria* strain 2.2 N.

It is contemplated that each disclosed methods can further comprise additional steps, manipulations, and/or components. It is also contemplated that any one or more step, manipulation, and/or component can be optionally omitted from the invention. It is understood that a disclosed methods can be used to provide the disclosed compounds. It is also understood that the products of the disclosed methods can be employed in the disclosed methods of using.

E. PHARMACEUTICAL COMPOSITIONS

In one aspect, the invention relates to pharmaceutical compositions comprising the disclosed compounds. That is, a pharmaceutical composition can be provided comprising a therapeutically effective amount of at least one disclosed compound or at least one product of a disclosed method and a pharmaceutically acceptable carrier.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, vaginal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein. In a preferred aspect, the compositions disclosed herein can be administered intraperitoneally. For example, during intraabdominal surgery (e.g., resection of an abcess), the disclosed compositions can be used as a wash. In this way, cells that were not excised and/or cells that may be unattached but still present in the body, can be killed upon readhereing.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

The disclosed compositions can be in solution, suspension (for example, incorporated into microparticles, liposomes, or cells). These can be targeted to a particular cell type via antibodies, receptors, or receptor ligands.

Pharmaceutical compositions of the present invention can be in a form suitable for topical or vaginal use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal or vaginal administration wherein the carrier is a solid. In one aspect, the mixture forms unit dose suppositories. Suitable carriers include cocoa butter and other materials commonly used in the art. The suppositories can be conveniently formed by first admixing the composition with the softened or melted carrier(s) followed by chilling and shaping in moulds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

Thus, the compositions can comprise, in addition to the disclosed compositions or for example, lipid or liposomal formulations, such as with cationic liposomes (e.g., DOTMA, DOPE, DC-cholesterol) or anionic liposomes. A lipid or liposomal formulation can further comprise proteins to facilitate cellular penetration, or targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al *Proc. Natl. Acad. Sci. USA* 84:7413-7417 (1987); U.S. Pat. No. 4,897,355. Furthermore, the compound can be administered as a component of a microcapsule where the diffusion of the compound or delivery of the compound from the microcapsule is designed for a specific rate or dosage.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

F. AGRICULTURAL COMPOSITIONS

In one aspect, the invention relates to agricultural compositions comprising the disclosed compounds. That is, a agricultural composition can be provided comprising a therapeutically effective amount of at least one disclosed compound or at least one product of a disclosed method and a agriculturally acceptable carrier.

In certain aspects, the disclosed agricultural compositions comprise the disclosed compounds (including agriculturally acceptable salt(s) thereof) as an active ingredient, a agriculturally acceptable carrier, and, optionally, other therapeutic ingredients or adjuvants. The instant compositions include those suitable for foliar or systemic administration.

The instant compounds may sprayed, atomized, dusted, scattered, coated, or poured on the subject, although the most suitable route in any given case will depend on the particular host, and nature and severity of the conditions for which the active ingredient is being administered. The agricultural compositions can be conveniently presented as an emulsion, paste, solution, powder, dust, granulate, polymeric encapsulation or combination and prepared by any of the methods well known in the art of agrichemicals.

As used herein, the term "agriculturally acceptable salts" refers to salts prepared from acceptable bases or acids. When the compound of the present invention is acidic, its corresponding salt can be conveniently prepared from agriculturally acceptable bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic bases include salts of primary, secondary, and tertiary amines, as well as cyclic amines and substituted amines such as naturally occurring and synthesized substituted amines. Other agriculturally acceptable organic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "agriculturally acceptable acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or agriculturally acceptable salts thereof, of this invention can be combined as the active ingredient in intimate admixture with a agriculturally acceptable carrier according to conventional agrochemical manufacturing techniques. The carrier can take a wide variety of forms depending on the form of preparation desired for administration, e.g., spraying or dusting. Thus, the agricultural compositions of the present invention can be presented as a powder for administration such as dusting. Further, the compositions can be presented as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or agriculturally acceptable salt(s) thereof, can also be administered by controlled release means and/or delivery devices. The compositions can be prepared by any of the methods of known in the art. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the agricultural compositions of this invention can include a agriculturally acceptable carrier and a compound or a agriculturally acceptable salt of the compounds of the invention. The compounds of the invention, or agriculturally acceptable salts thereof, can also be included in agricultural compositions in combination with one or more other therapeutically active compounds.

The agricultural carrier employed can be, for example, a solid or a liquid. Examples of such carriers include mineral substances, solvents, dispersants, wetting agents, tackifiers, thickeners, binders, or fertilizers. In preparing the compositions for administration, any convenient agricultural media can be employed. For example, the compositions may also contain further adjuvants such as stabilizers, antifoams, viscosity regulators, binders or tackifiers as well as fertilizers, micronutrient donors or other formulations for obtaining special effects. Optionally, whereas it is preferred to formulate commercial products as concentrates, whereas the end user will normally use dilute formulations.

The disclosed agricultural compositions can further comprise other therapeutically active compounds, which are usually applied in the treatment of the above the treatment or prevention of fungal infection from *Alternaria, Aspergillus,*

*Botrytis, Cercospora, Cercosporidium, Erysiphe, Geotrichum, Mycosphaerella, Mucor, Phoma, Phytophthora, Plasmopora, Pseudopeziza, Puccinia, Pythium, Rhizoctonia, Rhizopus, Septoria, Sporothrix, Stemphylium, Trichophyton,* and *Verticillium.*

It is understood that the disclosed compositions can be prepared from the disclosed compounds. It is also understood that the disclosed compositions can be employed in the disclosed methods of using.

G. METHODS OF USING THE COMPOSITION

1. Treatment Methods a. Pharmaceutical Treatments

The compounds disclosed herein are useful for treating, preventing, ameliorating, controlling or reducing the risk of a variety of conditions and/or diseases associated with fungal infection.

Fungal infections can manifest as superficial, cutaneous, or systemic infections. Examples of superficial or cutaneous classes of fungal infections include: dermatophytosis, dermatomycosis, onychomycosis, piedra, or candidiasis. Specific examples of superficial or cutaneous fungal infections include, but are not limited to: tinea capitis, tinea favosa, tinea corporis, tinea faciei, tinea pedis, tinea manuum, tinea imbricata, tinea cruris, tinea barbae, tinea nigra, tinea ungium, oral candidiasis, candidal vaginitis, candidal intertrigo, perianal candidiasis, candidal paronychia, erosio interdigitalis blastomycetica, chronic mucocutaneous candidiasis, and seborrhoeic dermatitis. Examples of systemic fungal infections include: aspergillosis, blastomycosis, invasive candidiasis, coccidioidomycosis, cryptococcosis, histoplasmosis, paracoccidioidomycosis, zygomycosis, and pneumocystosis. Typical fungal pathogen species infections may include: *Aspergillus, Candida, Cryptococcus, Histoplasma, Pneumocystis, Saccharomyces, Epidermophyton, Microsporum, Trichophyton, Scytalidium, Pityrosporum, Coccidioides, Histoplasma, Paracoccidioides, Blastomyces, Sporothrix, Candida, Trichosporon, Pneumocystis, Exophiala, Fonsecaea, Geotrichum, Pseudallescheria,* and *Rhizopus.*

Thus, in some aspects of the disclosed method, the fungal infection is tinea capitis, tinea favosa, tinea corporis, tinea faciei, tinea pedis, tinea manuum, tinea imbricata, tinea cruris, tinea barbae, tinea nigra, tinea ungium, oral candidiasis, candidal vaginitis, candidal intertrigo, perianal candidiasis, candidal paronychia, erosio interdigitalis blastomycetica, chronic mucocutaneous candidiasis, and seborrhoeic dermatitis. In a further aspect, the fungal infection is aspergillosis, blastomycosis, invasive candidiasis, coccidioidomycosis, cryptococcosis, histoplasmosis, paracoccidioidomycosis, zygomycosis, and pneumocystosis.

In one aspect, the invention relates to a method for the treatment of a fungal infection in a subject comprising the step of administering to the subject at least one disclosed compound or at least one disclosed product in a dosage and amount effective to treat the disorder in the subject. In a further aspect, the subject is a mammal, for example, a human. In a further aspect, the mammal has been diagnosed with a need for treatment of the disorder prior to the administering step. In a further aspect, the method further comprises the step of identifying a subject in need of treatment of the disorder. In a still further aspect, the fungal infection is cutaneous or superficial. In yet a further aspect, the fungal infection is systemic.

In one aspect, the method further comprises treating dermatophytosis, dermatomycosis, onychomycosis, piedra, or candidiasis. In further aspect, the treatment method further comprises treating tinea capitis, tinea favosa, tinea corporis, tinea faciei, tinea pedis, tinea manuum, tinea imbricata, tinea cruris, tinea barbae, tinea nigra, tinea ungium, oral candidiasis, candidal vaginitis, candidal intertrigo, perianal candidiasis, candidal paronychia, erosio interdigitalis blastomycetica, chronic mucocutaneous candidiasis, or seborrhoeic dermatitis. In a yet further aspect, the method further comprises treating aspergillosis, blastomycosis, invasive candidiasis, coccidioidomycosis, cryptococcosis, histoplasmosis, paracoccidioidomycosis, zygomycosis, or pneumocystosis.

In one aspect, the method further comprising the step of identifying the subject as having a need for treatment or prevention of fungal infection. In a further aspect, the subject (e.g., mammal) is immunocompromised or immunosuppressed.

In one aspect, the method further comprising treating a fungal infection from *Aspergillus, Candida, Cryptococcus, Histoplasma, Pneumocystis, Saccharomyces* or a combination thereof. In a further aspect, the fungal infection is from *Epidermophyton, Microsporum, Trichophyton, Scytalidium, Pityrosporum, Coccidioides, Histoplasma, Paracoccidioides, Blastomyces, Sporothrix, Candida, Cryptococcus, Trichosporon, Pneumocystis, Exophiala, Fonsecaea, Geotrichum, Pseudallescheria,* or *Rhizopus.*

In one aspect, the method further comprises the route of administration is oral, buccal, sublingual, nasal, topical, rectal, vaginal, parenteral or a combination thereof. In a further aspect, the route of administration is intramuscular, intravenous, intraocular, intraperitoneal, subcutaneous, or combination thereof.

In one aspect, the disclosed compositions can be administered by I.V., by injection and/or an I.V. drip.

For therapeutic uses, pharmaceutical compositions and formulations can contain an effective amount of active for treating the disorder. The specific effective amount for any particular subject will depend upon a variety of factors including the disorder being treated and the severity of the disorder; the identity and activity of the specific composition employed; the age, body weight, general health, sex and diet of the patient; the time of administration; the route of administration; the rate of excretion of the specific composition employed; the duration of the treatment; drugs used in combination or coincidental with the specific composition employed and like factors well known in the medical arts. For example, it is well within the skill of the art to start doses of a composition at levels lower than those required to achieve the desired therapeutic effect and to gradually increase the dosage until the desired effect is achieved. One can also evaluate the particular aspects of the medical history, signs, symptoms, and objective laboratory tests that are known to be useful in evaluating the status of a subject in need of attention for the treatment of ischemia-reperfusion injury, trauma, drug/toxicant induced injury, neurodegenerative disease, cancer, or other diseases and/or conditions. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: 1) a subject's physical condition is shown to be improved, 2) the progression of the disease or condition is shown to be stabilized, or slowed, or reversed, or 3) the need for other medications for treating the disease or condition is lessened or obviated, then a particular treatment regimen will be considered efficacious. If desired, the effective daily dose can be divided into multiple doses for purposes of administration. Consequently, single dose compositions can contain such amounts or submultiples thereof to make up the daily dose.

An effective amount of the composition can also be determined by preparing a series of compositions comprising varying amounts of the disclosed compounds and determining the release characteristics in vivo and in vitro and matching these characteristics with specific pharmaceutical delivery needs, inter alia, subject body weight, disease condition and the like.

The dosage for the compositions can be adjusted by the individual physician or the subject in the event of any counterindications. Dosage can vary, and can be administered in one or more dose administrations daily, for one or several days. Guidance can be found in the literature for appropriate dosages for given classes of pharmaceutical products.

The dosage ranges for the administration of the compositions are those large enough to produce the desired effect in which the symptoms disorder is affected. The dosage should not be so large as to cause adverse side effects, such as unwanted cross-reactions, anaphylactic reactions, and the like. Generally, the dosage can be 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, or 500 mg/kg, where any of the stated values can be upper of lower end points of a range.

Example dosages are disclosed herein. For example, when treating a subject with a fungal infection, or when preventing a fungal infection in a subject, the disclosed compounds or a pharmaceutically acceptable salt or hydrate thereof can be administered at a dosage of from 1 to about 500 mg/kg of the subject, can be administered at a dosage of from 10 to about 200 mg/kg of the subject, can be administered at a dosage of from 10 to about 100 mg/kg of the subject, or can be administered at a dosage of from 20 to about 500 mg/kg of the subject.

The compositions can be administered alone or combination with other antimicrobrial drugs. Combination therapy can present advantages over single-agent therapies: lower treatment failure rate, lower case-fatality ratios, slower development of resistance and consequently, less money needed for the development of new drugs. Antimicrobrial drugs include. The disclosed compounds can also be administered in combination with surgery. For example, the disclosed compounds can be administered prior to, during or after surgery. Administration during surgery can be as a bathing solution for the operation site. The resected part can also be bathed in the disclosed compounds.

It is contemplated that the disclosed compounds can be adminstered before, simultaneously, or after the administration of one or more additional antimicrobial agents. While not wishing to be bound by theory, it is believed that the disclosed compounds, in combination with one or more chemotherapeutic drugs, can have an augmented or synergystic effect on the subject. Further, the disclosed compounds, in combination with one or more antimicrobial drugs, can be individually given in dosages lower than the one or more antimicrobial drugs would be typically adminstered as single-agent therapies.

The disclosed compositions can also be employed to prevent fungal infection in a subject, such as in immunocomprimised patients. In one aspect, such a method comprises administering to the subject a prophylactically effective amount of or a pharmaceutically acceptable salt or hydrate thereof. It is understood that the dosage and/or frequency needed to prevent (i.e. maintenance dose) may be less (e.g., once vs. twice daily) of the dosage (e.g., half) needed to effect treatment of a fungal infections. Thus, in maintenance, a suitable dosage of the disclosed compounds or a pharmaceutically acceptable salt or hydrate thereof can be from 0.5 to about 250 mg/kg of the subject, can be administered at a dosage of from 5 to about 100 mg/kg of the subject, can be administered at a dosage of from 5 to about 50 mg/kg of the subject, or can be administered at a dosage of from 10 to about 250 mg/kg of the subject.

b. Agricultural Treatment

The compounds disclosed herein are useful for treating, preventing, ameliorating, controlling or reducing the risk of a variety of conditions and/or diseases associated with fungal infection.

Fungal infections can be various fungal microorganisms including, but not limited to: *Botrytis, Mycosphaerella, Cercospora, Rhizoctonia, Monilinia, Phytophthora, Alternaria, Aspergillus, Pseudocercosporella, Cladosporium, Chaetomium, Fusarium*, or *Colletotrichum*.

In one aspect, the invention relates to a method for the treatment or prevention of fungal infection in a plant, comprising administering to the plant an effective amount of the disclosed compound. In a further aspect, the method further comprises the step of identifying the plant as having a need for treatment or prevention of fungal infection.

In one aspect, the invention relates to a method for the treatment or prevention of fungal infection in a plant, comprising administering to the plant an effective amount of the disclosed compound where the fungal microorganism is from *Alternaria, Aspergillus, Botrytis, Cercospora, Cercosporidium, Erysiphe, Geotrichum, Mycosphaerella, Mucor, Phoma, Phytophthora, Plasmopora, Pseudopeziza, Puccinia, Pythium, Rhizoctonia, Rhizopus, Septoria, Sporothrix, Stemphylium, Trichophyton*, and *Verticillium*.

In one aspect, the method further comprises an amount of the disclosed compounds that is therapeutically effective. In a further aspect, the method comprises an amount that is prophylactically effective.

In one aspect, the invention relates to a method for the treatment or prevention of fungal infection in a plant, comprising administering to the plant an effective amount of the disclosed compound where the compound is application is foliar. In a further aspect, the method of application is systemic. In a still further aspect, the method of application is to the soil. In yet a further aspect, the method of application is to the seeds.

In one aspect, the invention relates to a method for the treatment or prevention of fungal infection in a plant, further comprising administration the disclosed compounds by spraying, atomizing, dusting, scattering, coating, or pouring.

In one aspect, the invention relates to a method for the treatment or prevention of fungal infection in a plant, comprising administering to the plant an effective amount of the disclosed compound where the plant is corn, soybean, wheat, rice, alfalfa, sorghum, peanut, tobacco, cotton, flax, safflower, oats, and canola; fruits and vegetables such as tomato, pepper, cucumber, lettuce, green beans, lima beans, peas, cantaloupe, musk melon, citrus fruits, grapes, and banana; and ornamentals and cut flowers such as geraniums, azaleas, roses, tulips, petunias, orchids, carnations, poinsettias, chrysanthemums; and conifers such as pine, yew, spruce.

For therapeutic uses, agricultural compositions and formulations can contain an effective amount of active ingredient for treating the disorder. The specific effective amount for any particular subject will depend upon a variety of factors including the disorder being treated and the severity of the disorder; the identity and activity of the specific composition employed; the time of administration; the route of administration; the duration of the treatment; agents used in combination or coincidental with the specific composition employed and like factors well known in the agricultural arts.

An effective amount of the composition can also be determined by preparing a series of compositions comprising varying amounts of the disclosed compounds and determining the release characteristics in vivo and in vitro and matching these characteristics with specific delivery needs, disease conditions and the like.

As used herein, an "effective" dose or regime of treatment with the disclosed composition against a particular fungal pathogen is one whose application achieves at least 20%, in a further aspect at least 50%, in a still further aspect at least 80%, and a yet further aspect at least 90%, disease control against that pathogen. An effective dose or regime may be achieved by adjusting the level of active ingredient(s) in the composition and/or the amount or frequency of compositions is applied.

The rates of application are can be about 5 g to about 2 kg of active ingredient (a.i.) per hectare (ha). In a further aspect, the rate is about from 10 g to about 1 kg a.i./ha. In a still further aspect, the rate is about from 20 gm to about 600 gm a.i./ha. Ranges for the administration of the compositions are those large enough to produce the desired effect in which the symptoms of the disorder is affected. The dosage should not be so large as to cause adverse side effects, such as toxicity or death.

c. Environmental Treatment

In one aspect, the invention relates to a method for the inhibiting fungal growth on a surface comprising the step of applying to the surface at least one disclosed compound or at least one disclosed product in a dosage and amount effective to inhibit fungal growth. In a further aspect, the method further comprises the step of identifying fungus on the surface prior to application. In a further aspect, the compound is cytoxic to the fungus.

In one aspect, the method further comprises application to wood, paper, plastic, metal, stone, natural and synthetic composite, natural and synthetic fabric, or leather. In a further aspect, the surface is heating, ventilation, and air-conditioning (HVAC) surfaces, insulation, wall-board, kitchen surfaces, bathroom surfaces, or other surface found in a building. In a still further aspect, the surface is found in a commercial or residential building.

2. Manufacture of a Medicament

The present invention is further directed to a method for the manufacture of a medicament for treating fungal infections (e.g., treatment of one or more skin and/or systemic infections associated with fungal pathogens) in subjects (e.g., mammals, e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

3. Kits

In one aspect, the invention relates to a kit comprising a disclosed compound or a product of a disclosed method and one or more of at least one agent known to inhibit fungal growth; at least one agent known to increase fungal growth; at least one agent known to treat a fungal infection; at least one agent known to treat a disease of uncontrolled fungal cell proliferation; or instructions for treating a disorder associated with fungal infections. In a further aspect, the at least one compound or the at least one product and the at least one agent are co-formulated. In a further aspect, the at least one compound or the at least one product and the at least one agent are co-packaged.

In a further aspect, the kit comprises a disclosed compound or a product of a disclosed method.

In a further aspect, the at least one compound and the at least one agent are co-formulated. In a still further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using, and/or the disclosed compositions.

4. Non-Medical Uses

Also provided are the uses of the disclosed compounds and products as pharmacological tools in the development and standardization of in vitro and in vivo test systems for the evaluation of the antifungal activity or, as part of the search for new antifungal agents. In a further aspect, the invention relates to the use of a disclosed compound or a disclosed product as pharmacological tools in the development and standardization of in vitro and in vivo test systems for the evaluation of antifungal activity as part of the search for new therapeutic agents or treatment protocols.

H. COMPOSITIONS WITH SIMILAR FUNCTIONS

It is understood that the compositions disclosed herein have certain functions, such as antifungal activities or anti-proliferative activities. Disclosed herein are certain structural requirements for performing the disclosed functions, and it is understood that there are a variety of structures which can perform the same function which are related to the disclosed structures, and that these structures will ultimately achieve the same result, for example, inhibition of fungal cell proliferation.

I. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases are commercially available, or can be prepared according to literature procedures or as illustrated herein.

The following exemplary compounds of the invention were synthesized. The Examples are provided herein to illustrate the invention, and should not be construed as limiting the invention in any way.

1. General Methods

Cultures obtained from *B. ambifaria* 2.2N strain were isolated from spray-dried cells, for example, by sequential solvent extraction with dichloromethane, 2-propanol and 2-propanol:$H_2O$. Optionally, the fractions may be further purified, for example on an open $C_{18}$ column. Optionally, the compounds can be further purified, for example by reverse phase HPLC. Further purification of the compounds resulted in essentially pure product.

2. Fermentation of *Burkholderia*

Compounds of the present invention can be produced by culturing the previously discussed microorganism in an an aqueous nutrient medium containing sources of carbon and nitrogen. Sources of carbon in the nutrient medium can include carbohydrates such as sucrose, glucose, glycerol, and the like. The exact quantity and number of carbon source(s) will vary, and will depend on, including but not limited to, other constituents in the medium, desired growth rate, and the like. Sources of nitrogen can include amino acids such as glycine, proline, methionine, and the like. An example of the process for production of the compounds of the present invention comprises inoculating the microorganism into a suitable culture medium, and then culturing under aerobic conditions. In one example, the disclosed compounds may be isolated from the aerobic fermentation of a culture of *Bulkholderia ambifaria*.

(1) Example 1

Initial growth studies of the 2.2 N strain were completed in 2 different media (¼ strength Tryptic Soy Broth (TSB)+0.2% Sucrose and ¼ strength TSB) and specific growth rate and doubling time were determined. Working stock culture was prepared in ¼ strength TSB+0.2% Sucrose media and used as inocula for future experiments. Initial shake flask experiments were completed using three production media to evaluate anti-fungal yield and variability. The production media tested were: ¼ strength TSB+0.2% Sucrose; ¼ strength TSB+0.2% Glucose; and KB20 media with glycerol. Anti-fungal material, with complete inhibition at 20 ppm in petri-dish study against *Botrytis* was isolated using ¼ strength TSB+0.2% Sucrose media. This media was selected for further studies in shake flask experiments.

Process scale-up evaluations were carried in 7.5 L fermentors with 5 L working volume. Various process conditions were tested to determine optimal production environment, including media (¼ strength TSB+0.2% Sucrose; ¼ strength TSB+0.2% Glucose; and KB20 media), pH (6 & 7), agitation (120 and 250 rpm), dissolved oxygen set at 20% (cascaded to agitation). All the fermentation batches were heat-killed before spray-drying or freeze-drying. Different temperatures (range from 50-121° C.) were tested to study the heat-stability of the active ingredient and establish optimal conditions to heat-kill the bacteria while maintaining 100% anti-fungal activity. Heat treatment at 80° C. for 10 min resulted in 100% anti-fungal activity. Increase in temperature to 100° C. resulted in substantial loss of activity.

Relatively high load of variant forms in the culture streaked from the fermentor was noticed. The original 2.2N strain was purified and separated amber colored and mucoid variant by repeated streaking on agar plates. The purified strain do not show any improvement in the anti-fungal activity compared to original strain. However, mucoid variant form resulted in very low to no activity.

The fermentation broth was initially spray-dried at an Inlet temperature of 150-160° C. and lower outlet temperature of 60-65° C. compared to an outlet temperature of 85-100° C. Different batches were then tested for freeze-drying (to preserve the heat-labile antifungal activity) to determine whether continuous exposure to higher temperature during spray-drying resulted in lower activity. Spray-drying and freeze-drying method for product recovery do not show any significant difference in activity. The heat-killed fermentation broth was concentrated using a Rotary evaporator and spray-dried to produce concentrated material. The heat-treated controls and concentrated product yielded from the Rota-yap were very active with complete inhibition of *Botrytis* at 20 ppm. Additionally, untreated fermentation culture broth resulted in higher product yield. Filter-sterilized culture supernatant resulted in very low to no activity. Cell breakage using sonicator did not show any increase in activity, which was similar to the untreated control. Sonication for a longer period of time resulted in heat generation and further degradation of the active ingredient, indicating scale-up of sonication is not a feasible technology.

(2) Example 2

Working stock cultures of strain 2.2 N were first prepared in an aqueous nutrient medium consisting of 1.5% (w/v) Tryptic Soy Broth (TSB), 0.2% (w/v) sucrose, 0.25% (w/v) $K_2HPO_4$, and 0.5% (w/v) $NH_4Cl$. Cultures (250 L) were produced in 300 L working volume fermenters. The inocula were staged from 100 mL to 25 L in the same medium in 10-fold increasing increments. Cultures were incubated for 32 h at 30° C. with aeration maintained at 30% dissolved oxygen, and pH 6 was maintained by addition of 17% (v/v) $NH_4OH$. Cells were recovered by centrifugation (5000×g) in a continuous flow centrifuge and cell pastes packaged in plastic bags and frozen. Cell pastes were defrosted, adjusted to 30% moisture content by addition of water, and spray dried at an inlet temperature of 170° C. and outlet temperature of 100° C. The dried product moisture content was 5%.

3. Extraction and Isolation of Compounds a. Example 1

A slurry of spray dried cells (35 g) in dichloromethane (DCM, 400 mL) was stirred at room temperature for 20 h. The slurry was filtered through 3 cm bed of celite and washed with DCM (200 mL). The solid residue was stirred with 2-propanol (350 mL) for 1 h. The solvent was removed by vacuum filtration and the residue was stirred with 2-propanol:$H_2O$ (30:70, 400 mL) for 12 h at room temperature. The resulting suspension was transferred to twelve 50 mL-Falcon tubes and centrifuged for 1 h at 4000 rpm. The supernatant was discarded and the pellets were combined and dissolved in acetonitrile:water (1:1) (100 mL). Lyophilization of this suspension gave 5.3 g crude extract. 1 g crude extract was suspended in methanol:DCM (80:20, 25 mL), then centrifuged for 1 h at 4000 rpm. The supernatant was discarded and the remaining solid was suspended in 20 mL $H_2O$ and lyophilized to give 250 mg extract enriched with burkholdines (presently disclosed compounds). The bacterial extract (250 mg) was suspended in a volume of 1.5 mL water with 2% acetonitrile and applied to the top of an open $C_{18}$ column. The column was eluted with a gradient of acetonitrile-water (2%, 10%, 25%, 50% and 100%) and five fractions were collected (F1-F5).

According to LC/MS, F4 (8.5 mg) was found to be highly enriched in a mixture of burkholdines. F4 was further purified by reversed phase high pressure liquid chromatography (RP-HPLC) using preparative Atlantis-T3 column (10 mm×250 mm). Compounds were eluted with a linear gradient from 95% solvent A (0.07% trifluoroacetic acid in water) to 60% solvent B (0.07% trifluoroacetic acid in acetonitrile) over 95 min at 5 mL/min. The eluent was monitored at 205 nm and peaks at 59 min (Bk-1229) were collected and lyophilized to yield Bk-1229 (400 µg) as off-white powder.

Bk-1229 (1): UV (CH$_3$CN:H$_2$O 1:1) $\lambda_{max}$ nm (log ε) 230 (1.54), 274 (1.08); IR (KRS-5 cell, acetonitrile) $\nu_{max}$ 3274, 2919, 1698, 1683, 1670, 1652, 1635, 1558, 1540, 1519, 1507 cm$^{-1}$; $^1$H and $^{13}$C NMR, see Tables 1 and 2; HRESIMS [M+H]$^+$ m/z 1230.5746 (calcd for C$_{52}$H$_{84}$N$_{11}$O$_{23}$, 1230.5735, 0.3 ppm).

a. Example 2

Isolation of Compound 2

A slurry of spray dried cells (35 g) in dichloromethane (DCM, 400 mL) was stirred at room temperature for 20 h. The slurry was filtered through 3 cm bed of celite and washed with DCM (200 mL). The solid residue was stirred with 2-propanol (350 mL) for 1 h. The solvent was removed by vacuum filtration and the residue was stirred with 2-propanol:H$_2$O (30:70, 400 mL) for 12 h at room temperature. The resulting suspension was transferred to twelve 50 mL-Falcon tubes and centrifuged for 1 h at 4000 rpm. The supernatant was discarded and the pellets were combined and dissolved in acetonitrile:water (1:1) (100 mL). Lyophilization of this suspension gave 5.3 g crude extract. 1 g crude extract was suspended in methanol:DCM (80:20, 25 mL), then centrifuged for 1 h at 4000 rpm. The supernatant was discarded and the remaining solid was suspended in 20 mL H$_2$O and lyophilized to give 250 mg extract enriched with burkholdines. The bacterial extract (250 mg) was suspended in a volume of 1.5 mL water with 2% acetonitrile and applied to the top of an open C$_{18}$ column. The column was eluted with a gradient of acetonitrile-water (2%, 10%, 25%, 50% and 100%) and five fractions were collected (F1-F5). According to LC/MS, F4 (8.5 mg) was found to be highly enriched in a mixture of burkholdines. F4 was further purified by reversed phase high pressure liquid chromatography (RP-HPLC) using preparative Atlantis-T3 column (10 mm×250 mm). Compounds were eluted with a linear gradient from 95% solvent A (0.07% trifluoroacetic acid in water) to 60% solvent B (0.07% trifluoroacetic acid in acetonitrile) over 95 min at 5 mL/min. The eluent was monitored at 205 nm and peaks at 64 min (Bk-1097) were collected and lyophilized to yield Bk-1097 (300 µg) as off-white powder.

Bk1097 (2): UV (CH$_3$CN:H$_2$O 1:1) $\lambda_{max}$ nm (log ε) 232 (1.48), 276 (1.09); IR (KRS-5 cell, acetonitrile) $\nu_{max}$ 3273, 2920, 1669, 1651, 1635, 1557, 1539, 1519, 1507 cm$^{-1}$; $^1$H and $^{13}$C NMR, see Tables 1 and 3; HRESIMS [M+H]$^+$ m/z 1098.5321 (calcd for C$_{47}$H$_{76}$N$_{11}$O$_{19}$, 1098.5313, 0.2 ppm).

TABLE 1

HSQC ASSIGNMENTS

| | 1: Bk-1229 | | | 2: Bk-1097 | | |
|---|---|---|---|---|---|---|
| No | δC | δH | Assignment | No | δC | δH | Assignment |
| 1 | 13.5 | 0.84 | C18-CH3 FAA | 1 | 13.4 | 0.84 | C18-CH3 FAA |
| 2 | 21-35 | 1.24 | (C9-C17)-CH2 FAA | 2 | 21-31 | 1.21 | (C9-C17)-CH2 FAA |
| 3 | 29.6 | 1.53 | C8-CH2 FAA | 3 | 32.9 | 1.35-1.40 | C8-CH2 FAA |
| 4 | 36.2 | 2.38 | β Asn II | 4 | 36.3 | 2.38 | β Asn II |
| | | 2.42 | β Asn I | | | 2.43 | β Asn I |
| | | 2.58 | β Asn I | | | 2.58 | β Asn I |
| | | 2.62 | β Asn II | | | 2.62 | β Asn II |
| 5 | 38.4 | 1.34 | C4-CH2 FAA | 5 | 38.6 | 1.34 | C4-CH2 FAA |
| | | 1.77 | | | | 1.75 | |
| 6 | 40.3 | 2.30 | C2-CH2 FAA | 6 | 40.4 | 2.31 | C2-CH2 FAA |
| | | 2.41 | | | | 2.41 | |
| 7 | 41.6 | 3.55 | α Gly | 7 | 41.3 | 3.56 | α Gly |
| | | 3.84 | | | | 3.83 | |
| 8 | 43.6 | 4.20 | C3-CH FAA | 8 | 43.7 | 4.19 | C3-CH FAA |
| 9 | 49.3 | 4.56 | α Asn I | 9 | 49.3 | 4.56 | α Asn I |
| 10 | 49.4 | 4.49 | α Asn II | 10 | 49.5 | 4.49 | α Asn II |
| 11 | 54.5 | 4.30 | α Ser I | 11 | 54.7 | 4.30 | α Ser I |
| 12 | 54.7 | 4.05 | α Ser II | 12 | 54.9 | 4.09 | α Ser II |
| 13 | 54.8 | 4.63 | α HydroxyAsn | 13 | 55.0 | 4.61 | α HydroxyAsn |
| 14 | 59.9 | 4.04 | α HydroxyTyr | 14 | 60.0 | 4.05 | α HydroxyTyr |
| 15 | 60.5 | 3.46 | β Ser II | 15 | 60.6 | 3.45 | β Ser II |
| 16 | 61.1 | 3.59 | β Ser I | 16 | 61.1 | 3.58 | β Ser I |
| 17 | 65.2 | 3.04 | C5 Xylose C5 | 17 | 67.0 | 3.43 | C5-CH FAA |
| 18 | 60.5 | 3.48 | C5-CH FAA | 18 | 68.4 | 3.60 | C7-CH FAA |
| 19 | 68.9 | 3.33 | C4 Xylose | 19 | 70.3 | 4.97 | β HydroxyTyr |
| 20 | 70.1 | 4.96 | β HydroxyTyr | 20 | 71.4 | 3.96 | β HydroxyAsn |
| 21 | 71.2 | 3.96 | β HydroxyAsn | 21 | 75.3 | 2.92 | C6-CH FAA |
| 22 | 72.5 | 3.98 | C2 Xylose | 22 | 414.1 | 6.65 | C3 C5 HydroxyTyr |
| 23 | 73.7 | 3.06 | C6-CH FAA | 23 | 326.5 | 7.12 | C2 C6 HydroxyTyr |
| 24 | 75.9 | 3.09 | C3 Xylene | | | | |
| 25 | 76.4 | 3.72 | C7-CH FAA | | | | |
| 26 | 101.27 | 4.17 | C1 Xylene | | | | |
| 27 | 134.1 | 6.64 | C3 C5 HydroxyTyr | | | | |
| 28 | 126.6 | 7.12 | C2 C6 HydroxyTyr | | | | |

TABLE 2

HMBC AND ROESY CORRELATIONS FOR BK-1229 (1) IN DMSO-D6 (600 MHz).

| | δC | δD | HMBC | ROESY | | | | | |
|---|---|---|---|---|---|---|---|---|---|
| β-HydroxyTyr | | | | | | | | | |
| A | 59.9 | 4.04 | | β | NH | C2—H, C6—H | | | |
| B | 70.1 | 4.96 | | α | β-OH | C2—H, C6—H | | | |
| β-OH | | 5.65 | α | β | C2—H, C6—H | OH | | | |
| C1 | 131.7 | | NA | α | OH | | | | |
| C2 and C6 | 126.6 | 7.12 | β, C2, C4, C6 | OH | β | β-OH | NH | C3—H, C5—H | |
| C3 and C5 | 114.1 | 6.64 | C1, C3, C4, C5 | β-OH | C3—H, C5—H | | | | |
| C4 | 155.8 | | | β-OH | C2—H, C6—H | | | | |
| OH | | 9.25 | C3, C4, C5 | NH (Gly) | | | | | |
| NH | | 7.82 | | | | | | | |
| C=O | 170.6 | | β-C=O, γ-C=O | | | | | | |
| Asn I | | | | | | | | | |
| A | 49.3 | 4.56 | α-C=O, γ-C=O | 2.58 | γ-NH2 | | α (Ser I) | α | |
| β | 36.2 | 2.42 | | 2.42 | | | | | β |
| | | 2.58 | | | | | | | |
| γ-C=O | 170.4 | | NA | | | | | | |
| γ-NH2 | | 6.91 | β | 7.34 | β | | | | |
| | | 7.34 | γ-C=O | 6.91 | β | | | | |
| NH | | 7.34 | C=O (β-HydroxyTyr) | α | | | α-Hydroxy-Tyr | | |
| C=O | 167.6 | | NA | | | | | | |
| Gly | | | | | | | | | |
| A | 41.6 | 3.55 | C=O | α | NH | | NH (Asn I) | | |
| | | 3.84 | | | | | | | |
| NH | | 7.66 | | α | α (Asn I) | | | | |
| C=O | 169.5 | | NA | | | | | | |

TABLE 2-continued

HMBC AND ROESY CORRELATIONS FOR BK-1229 (1) IN DMSO-D6 (600 MHz).

| | | | HMBC | ROESY | | | |
|---|---|---|---|---|---|---|---|
| Asn II | | | | | | | |
| A | 49.4 | 4.49 | β, C=O, γ-C=O | NH | NH (Ser I) | | |
| B | 36.2 | 2.38 | α, C=O, γ-C=O | 2.62 | NH | | |
| | | 2.62 | | 2.38 | | | |
| γ-C=O | 170.6 | | NA | 7.34 | γ-NH2 | | |
| γ-NH2 | | 6.91 | β | 6.91 | | | |
| | | 7.34 | γ-C=O | | | | |
| NH | | 8.34 | C=O (Gly) | α | β (Ser I) | NH (Ser I) | |
| C—O | 167.6 | | NA | | | | |
| Ser I | | | | | | | |
| A | 54.5 | 4.30 | β, C=O | NH | β | NH (β-HydroxyAsn) | |
| B | 61.1 | 3.59 | C=O | NH | α | NH (β-HydroxyAsn) | |
| OH | | 4.79 | α, β | NH | β | OH | |
| NH | | 7.75 | NA | α | β | OH | β (Asn II) | α (Asn II) |
| C—O | 169.4 | | NA | | | | |
| β-HydroxyAsn | | | | | | | |
| A | 54.8 | 4.63 | C=O | NH | β | NH (tAA) | |
| B | 71.2 | 3.96 | α, C=O, γ-C=O | α | β-OH | γ-NH2 | |
| β-OH | | 5.62 | α, β, γ-C=O | β | γ-NH2 | | |
| γ-C=O | 172.6 | | NA | | | | |
| γ-NH2 | | 6.8 | | 7.2 | β | β-OH | |
| | | 7.2 | | 6.8 | | | |
| NH | | 7.80 | C=O (Ser I) | α | β | β-OH | NA (tAA) | α (Ser I) | β (Ser I) |
| C—O | 166.5 | | NA | | | | |

TABLE 2-continued

HMBC AND ROESY CORRELATIONS FOR BK-1229 (1) IN DMSO-D6 (600 MHz).

| FAA | 13C | 1H | HMBC | C3-CH | α (Hydroxy-Asn) | NH (Hydroxy-Asn) | NH (Ser-I) | NH (Ser-II) |
|---|---|---|---|---|---|---|---|---|
| NH | | 7.32 | | C3-CH | | | | |
| C1-C=O | 170.5 | | NA | | | | | |
| C2-CH2 | 40.3 | 2.30, 2.41 | C=O | C3-CH | C4-CH2 | C4-CH2 | | |
| C3-CH | 43.6 | 4.20 | | NH | C2-CH2 | C2-CH2 | | NH (Ser-II) |
| C4-CH2 | 38.4 | 1.34, 1.77 | | 1.77, 1.34 | C5-OH | C6-CH | NH (Ser-I) | |
| | | | | | C5-OH | C6-OH | | |
| C5-CH | 66.5 | 3.48 | C4-CH2, C5-CH, C6-CH | C4-CH2 | | | C5-OH | |
| C5-OH | | 4.06 | | | | | C3-OH | |
| C6-CH | 73.7 | 3.06 | C7-CH | C6-OH | C4-CH2 | | | |
| C6-OH | | 4.12 | C5-CH, C6-CH, C7-CH | C4-CH2 | C5-CH | | | |
| C7-CH | 76.4 | 3.72 | | C6-OH | C5-OH | C5-CH | C8-CH2 | |
| C8-CH2 | 29.6 | 1.53 | | C7-CH | C6-CH | C6-OH | | (C9-C17)-CH2 |
| (C9-C17)-CH2 | (21-35) | 1.24 | C18-CH3 | C18-CH3 | C8-CH2 | C6-CH | C7-CH | (C9-C17)-CH2 |
| | | | | | | | C2-OH-Xx | C1-CH-Xx |
| C18-CH3 | 13.5 | 0.85 | (C9-C17)-CH2 | (C9-C17)-CH2 | | | | C1-CH-Xx |
| | | | | | | | C2-OH-Xx | C1-CH-Xx |

TABLE 2-continued

HMBC AND ROESY CORRELATIONS FOR BK-1229 (1) IN DMSO-D6 (600 MHz).

| Ser II | | | | | | | |
|---|---|---|---|---|---|---|---|
| A | 54.7 | 4.05 | | β | | CH2-CH2 (FAA) | |
| B | 60.5 | 3.46 | | OH | NH | NH (Tyr) | |
| OH | | 4.90 | α, β | β | NH | | |
| NH | | 8.09 | C=O (FAA) | α | OH | | NH (FAA) |
| C=O | 171.4 | | NA | | | | |
| Xylose (Xy) | | | | | | | C3-CH (FAA) |
| C1-CH | 101.2 | 4.17 | C7-CH | C7-CH=CH (FAA) | C6-CH (FAA) | C5-CH2 (FAA) | |
| C2-CH | 72.5 | 2.98 | C1-CH Xy | C2-OH Xy | C2-CH Xy | C3-CH2 Xy | C2-OH Xy |
| C2-OH | | 4.94 | C1-CH Xy | C1-CH Xy | | | |
| C3-CH | 75.9 | 3.09 | (C2-CH, C4-CH) Xy | C3-OH Xy | C4-CH Xy | | |
| C3-OH | | 4.93 | C3-CH Xy | C3-CH Xy | | | |
| C4-CH | 68.9 | 3.33 | (C4-CH, C5-CH2) Xy | C4-CH Xy | | | |
| C4-OH | | 4.92 | | | | | |
| | 65.2 | 3.04 | (C1-CH), C3-CH, C4-CH) Xy | 3.70 | C4-CH Xy | C1-CH Xy | |
| | | 3.70 | (C1-CH), C3-CH, C4-CH) Xy | 3.04 | C4-OH Xy | C3-OH Xy | C6-CH (FAA) |

*Highlighted regions show ROESY correlations between residues.

TABLE 3

HMBC AND ROESY CORRELATIONS FOR BK-1097 (2) IN DMSO-D6 (600 MHz).

| Assignment | δC | δH | J (HZ) | HMBC | ROESY | |
|---|---|---|---|---|---|---|
| β-Hydroxy Tyr | | | | | | |
| A | 60.0 | 4.05 | 4.0, 7.6 | | β | C2-H, C6-H |
| B | 70.3 | 4.97 | 4.0 | C2, C6 | α | C2-H, C6-H | β-OH
| β-OH | | 5.62 | 4.0 | α | β | C2-H, C6-H |
| C1 | 131.7 | | | NA | | |
| C2 and C6 | 126.5 | 7.12 | | β, C2, C4, C6 | α | C3-H, C5-H | β-OH
| C3 and C5 | 114.1 | 6.65 | | C1, C3, C4, C5 | | C2-H, C6-H | OH
| C4 | 156.1 | | | NA | | |
| OH | | 9.25 | | C3, C4, C5 | C3-H, C5-H | C2-H, C6-H |
| NH | | 7.88 | 7.6 | NA | α(Hydroxy Tyr) β-OH | |
| C=O | 170.4 | | | | α(Ser II) | |
| Asn I | | | | | | |
| α | 49.3 | 4.56 | 3.9, 5.7 | β, γ-C=O | β | |
| β | 36.3 | 2.43 | 3.9 | α, γ-C=O | 2.58 | |
| | | 2.58 | | | 2.43 | |
| γ-C=O | 171.0 | | | NA | | |
| γ-NH2 | | 6.92 | 3.8 | β, γ-C=O | 7.34 | |
| | | 7.34 | | γ-C=O | 6.92 | |
| NH | | 7.77 | 5.7 | C=O (Hydroxy Tyr) | α(Hydroxy Tyr) β | |
| C=O | 167.6 | | | NA | | |
| Gly | | | | | | |
| α | 41.3 | 3.56 | 3.9, 7.8 | C=O | 3.83 | NH
| | | 3.83 | | | 3.56 | |
| NH | | 7.69 | 7.8 | | α(Asn I) | |
| C=O | 169.8 | | NA | | | |

TABLE 3-continued

HMBC AND ROESY CORRELATIONS FOR BK-1097 (2) IN DMSO-D6 (600 MHz).

| | | | | | |
|---|---|---|---|---|---|
| Asn II | | | | | |
| α | 49.5 | 4.49 | 4.0, 5.9 | β, C=O | β | NH (Ser I) |
| β | 36.3 | 2.38 | 5.9 | α, C=O | α | NH |
| | | 2.62 | | | | γ-NH2 |
| γ-C=O | 171.1 | | | NA | | |
| γ-NH2 | | 6.92 | | β, γ-C=O | 7.34 | β |
| | | 7.34 | | γ-C=O | 6.92 | |
| NH | | 8.34 | 4.0 | NA | α | α (Gly) |
| C=O | 167.8 | | | | | |
| Ser I | | | | | | |
| α | 54.7 | 4.30 | 3.8, 5.9 | β, C=O | β | NH (HydroxyAsn) |
| β | 61.1 | 3.58 | 3.8 | α, C=O | α | OH |
| OH | | 4.81 | | β | β | NH |
| NH | | 7.76 | 5.9 | NA | β | α (Asn II) |
| C=O | 169.4 | | 4.0, 7.7 | | | |
| β-HydroxyAsn | | | | | | |
| α | 55.0 | 4.04 | | C=O, γ-C=O | β | NH (fAA) |
| β | 71.4 | 3.96 | 4.0 | α, C=O, γ-C=O | α | NH |
| β-OH | | 5.66 | 4.0 | α, β | β | NH |
| γ-C=O | 173.1 | | | NA | | |
| γ-NH2 | | 6.82 | | | 7.20 | β |
| | | 7.20 | | | 6.82 | β-OH |
| NH | | 7.82 | 7.7 | C=O (Ser I) | α | OH |
| C=O | 167.5 | | | NA | β | NH (fAA) |

TABLE 3-continued

HMBC AND ROESY CORRELATIONS FOR BK-1097 (2) IN DMSO-D6 (600 MHz).

| Position | 13C | 1H | J (Hz) | HMBC | ROESY | | |
|---|---|---|---|---|---|---|---|
| FAA | | | | | | | |
| NH | | 7.36 | 11.4 | C=O (Hydroxy Asn) | | | |
| C1-C=O | 170.5 | | | NA | | | |
| C2-CH2 | 40.4 | 2.31, 2.41 | 4.0, 7.6, 7.6 | C=O, C3-CH | C3-CH | | |
| C3-CH | 43.7 | 4.19 | 4.0, 11.4 | C=O | | | |
| C4-CH2 | 38.6 | 1.34, 1.75 | 4.0, 11.5, 7.7 | | | | |
| C5-CH | 67.0 | 3.43 | | C5-CH, C6-CH | C6-OH | C4-CH2 | C3-CH |
| C5-OH | | 4.40 | | C5-CH | C7-CH | C5-OH | C4-CH2 |
| C6-CH | 75.3 | 2.92 | 3.9, 7.6 | C5-CH, C6-CH | C8-CH2 | C9-CH2 | C6-CH |
| C6-OH | | 4.11 | 7.6 | | C7-OH | | |
| C7-CH | 68.4 | 3.60 | 3.9, 7.8 | C6-CH, C7-CH, C8-CH2 | C7-OH | C7-OH | C6-CH |
| C7-OH | | 4.04 | 3.9, 7.8 | | | | |
| C8-CH2 | 32.9 | 1.35, 1.40 | | | | | |
| (C9-C17)-CH2 | (21.6-30.7) | 1.24 | | C18-CH3 | CH2 (1.24) | | |
| C18-CH3 | 13.4 | 0.84 | 3.9 | (C9-C17)-CH2 | C18-C3 | | C6-CH |
| Ser II | | | | | | | |
| α | 54.9 | 4.09 | 3.9, 5.9 | β, C=O | NH | | |
| β | 60.6 | 3.45 | 5.9 | α | OH | | |
| OH | | 4.91 | | α | β | | |
| NH | | 8.09 | 3.9 | C=O (FAA) | C2-CH2 (FAA) | | C6-OH |
| | 170.9 | | | NA | | | |

*Highlighted regions show ROESY correlation between residues.

4. Analytical Methods $^1$H, $^1$H—$^1$H$_g$COSY, $^1$H—$^1$H dqfCOSY, $^1$H—$^1$H TOCSY, $^1$H—$^{13}$C HSQC, $^1$H—$^{13}$C HMBC, $^1$H—$^1$H ROESY, DEPT and $^{13}$C were carried out at 25° C. NMR data were collected using either a 500 MHz Varian INOVA-NMR spectrometer with a 3 mm Nalorac MDBG probe or 600 MHz Varian INOVA-NMR spectrometer with a cryoprobe with standard pulse sequences. The IR spectrum was recorded on a JASCO FTIR-420 spectrophotometer. UV spectra were recorded on an hp-8552A diode array spectrophotometer. Electrospray ionization mass spectrometry (ESI-MS), Liquid chromatography-mass spectrometry (LC/MS), and Fourier transform-ion cyclotron resonance (FT-ICR) were run at the University of Utah Mass Spectrometry and Proteomics Core Facility.

Figure 12:
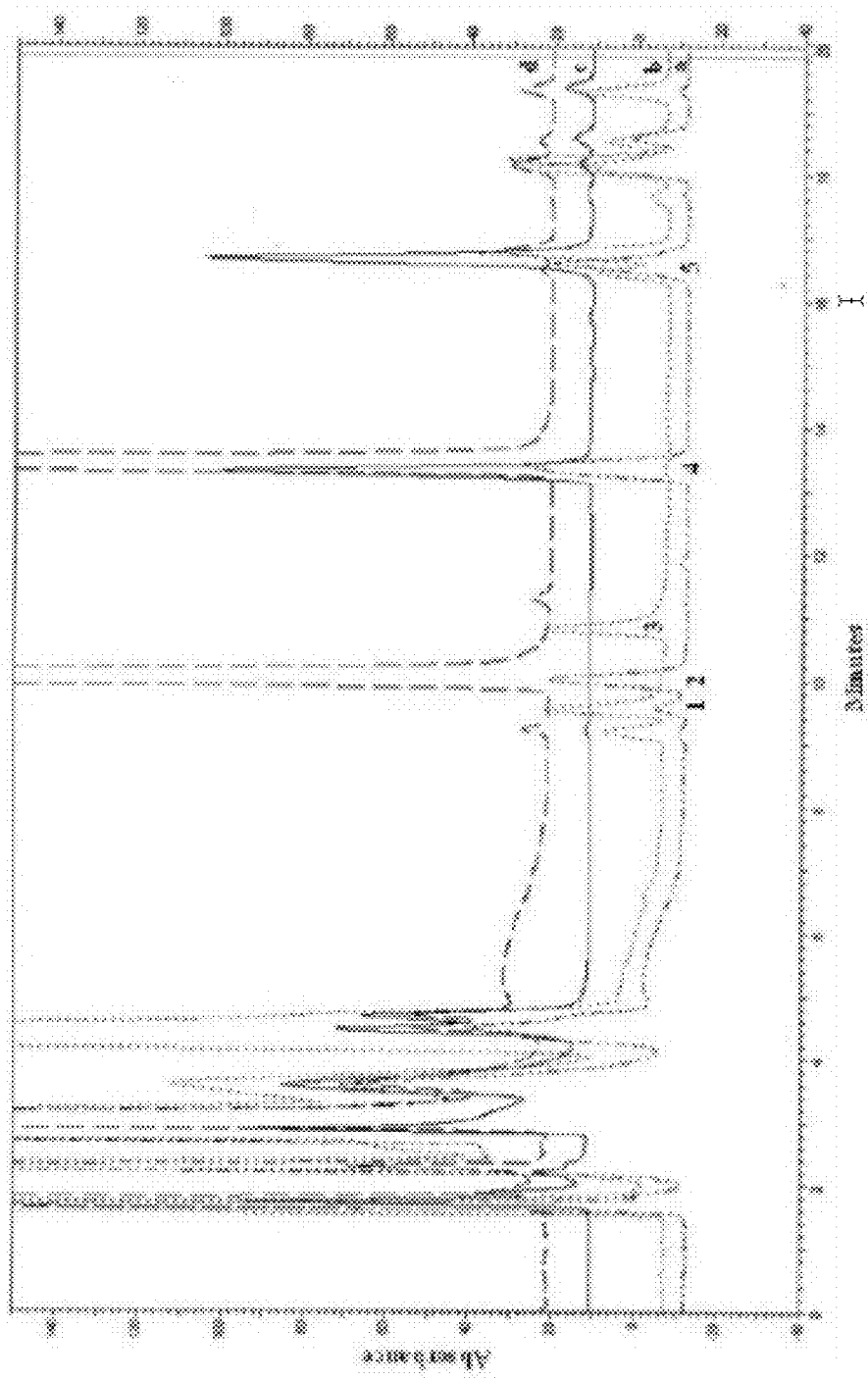
FIG. 12 shows HPLC analysis of FDAA derivatives of burkholdines. HPLC chromatograms of FDAA derivatives of: (a) burkholdines after acid hydrolysis, (b) DL-beta hydroxy Asp, (c) DL-Ser, (d) DL-Asp, showing (1) L-β-hydroxyAsp (9.5 min), (2) L-Asp (10 min), (3) D-β-hydroxyAsp (10.8 min), (4) D-Asp and L-Ser (13.4 min), (5) D-Ser (16.6 min).

Acid Hydrolysis and FDAA Analysis (Marfey's method) was performed on the presently disclosed compounds. In a thick walled microvial, Bk-1229 and Bk-1097 (100 μg each) were hydrolyzed in 250 μL of 6 N HCl containing 0.1% phenol (w/v). The vial was sealed and heated at 110° C. for 20 h. The reaction was allowed to cool and concentrated to dryness by lyophilization. The residue was dissolved in 100 μL water, and subsequently 300 μL of 1 M aqueous NaHCO3 and 250 μL of 1% (w/v) of Nα-(2,4-dinitro-5-fluorophenyl)-L-alaninamide (L-FDAA) in acetone were added. This mixture was heated at 50° C. for 1.5 h and then allowed to cool to room temperature. The L-FDAA derivatives were separated by RP-HPLC using a C18 column (4.6 mm×150 mm). A linear gradient of 10% acetonitrile in 0.1 M NH4OAc (pH 5) to 50% acetonitrile in 0.1 M NH4OAc over 60 min was used at 1 mL/min. The eluent was monitored at 340 nm (FIG. 12).

FDVA Derivatization of the Hydrolysate Burkholdines was then performed. The hydrolysate of Bk-1229 and Bk-1097 was obtained as described above and derivatized with 1% (w/v) of Nα-(2,4-dinitro-5-fluorophenyl)-L-valinamide (L-FDVA) in acetone. The reaction was heated at 40° C. for 1 h. The L-FDVA derivatives were separated by RP-HPLC as described before (FIG. 13).

Figure 13:
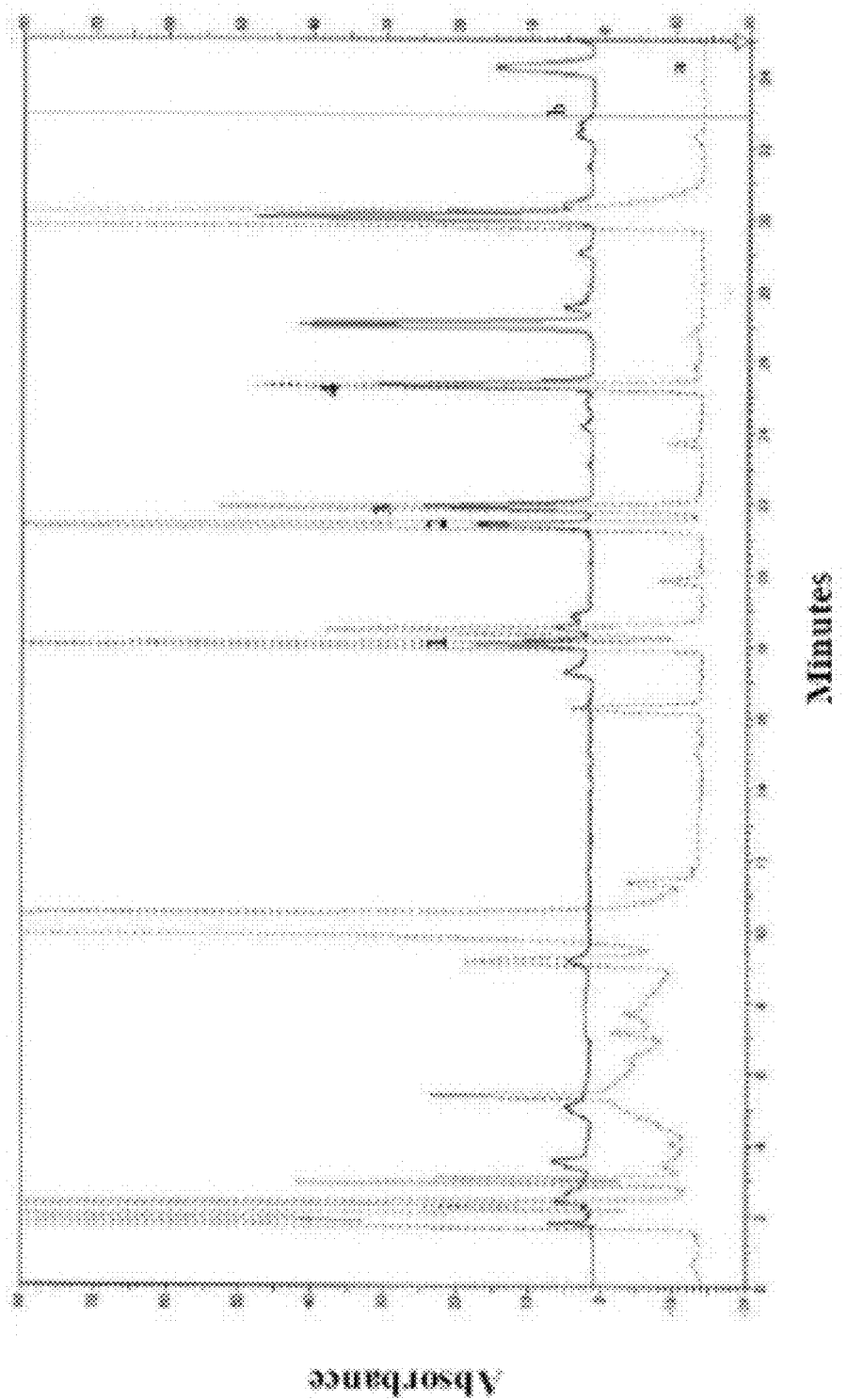
FIG. 13 shows HPLC analysis of FDVA derivatives of burkholdines. HPLC chromatograms of FDVA derivatives of: (a) DL-Asp/DL-Ser mixture, (b) burkholdines after acid hydrolysis, showing (1) L-Asp (18 min), (2) D-Asp (21.3 min), (3) L-Ser (21.9 min), (4) D-Ser (25.3 min).

Comparing the retention times of FDAA derivatives of L and DL standard amino acids and the hydrolysate of burkholdines, L-Hydroxy-Asp (9.5 min), L-Asp (10 min), D-Asp (13.4 min), L-Ser (13.4 min), D-Ser (16.6 min) and Gly (18.3 min) were detected. D-Asp and L-Ser peaks overlapped. Burkholdines were derivatized with L-FDVA and both D-Asp (21.3 min) and L-Ser (21.9 min) were identified (FIGS. 12 and 13).

Figure 14:
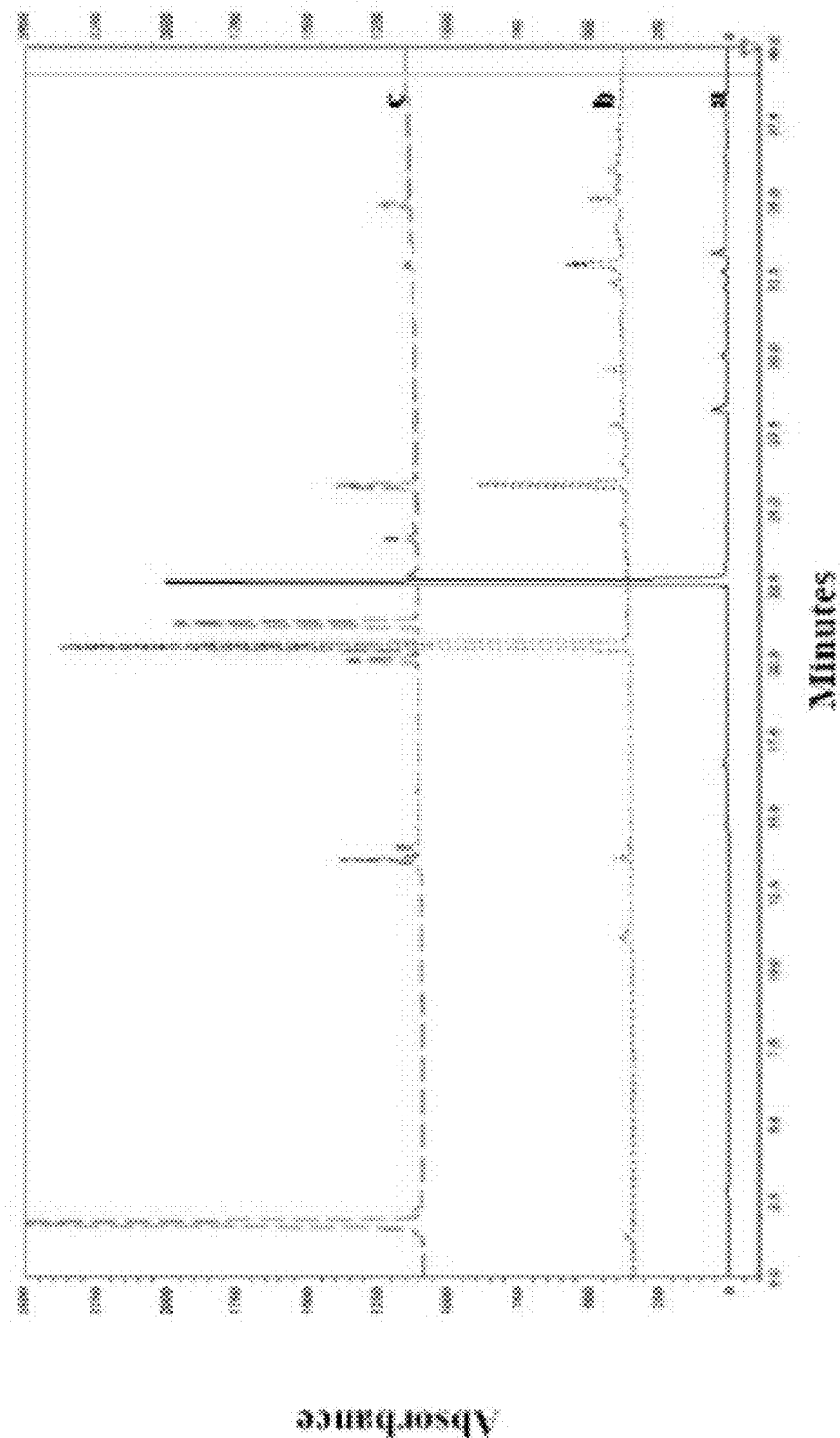
FIG. 14: HPLC analysis of dinitrobenzyl (DNB-F) derivative of burkholdines showing the presence of L-Ser-L-Asn residue, including HPLC chromatogram of dinitrobenzyl derivative of: (a) L-Ser-D-Asn (22.7 min), (b) L-Ser-L-Asn (20.6 min), (c) formic acid hydrolysate of burkholdines (20.6 min).
Figure 15:
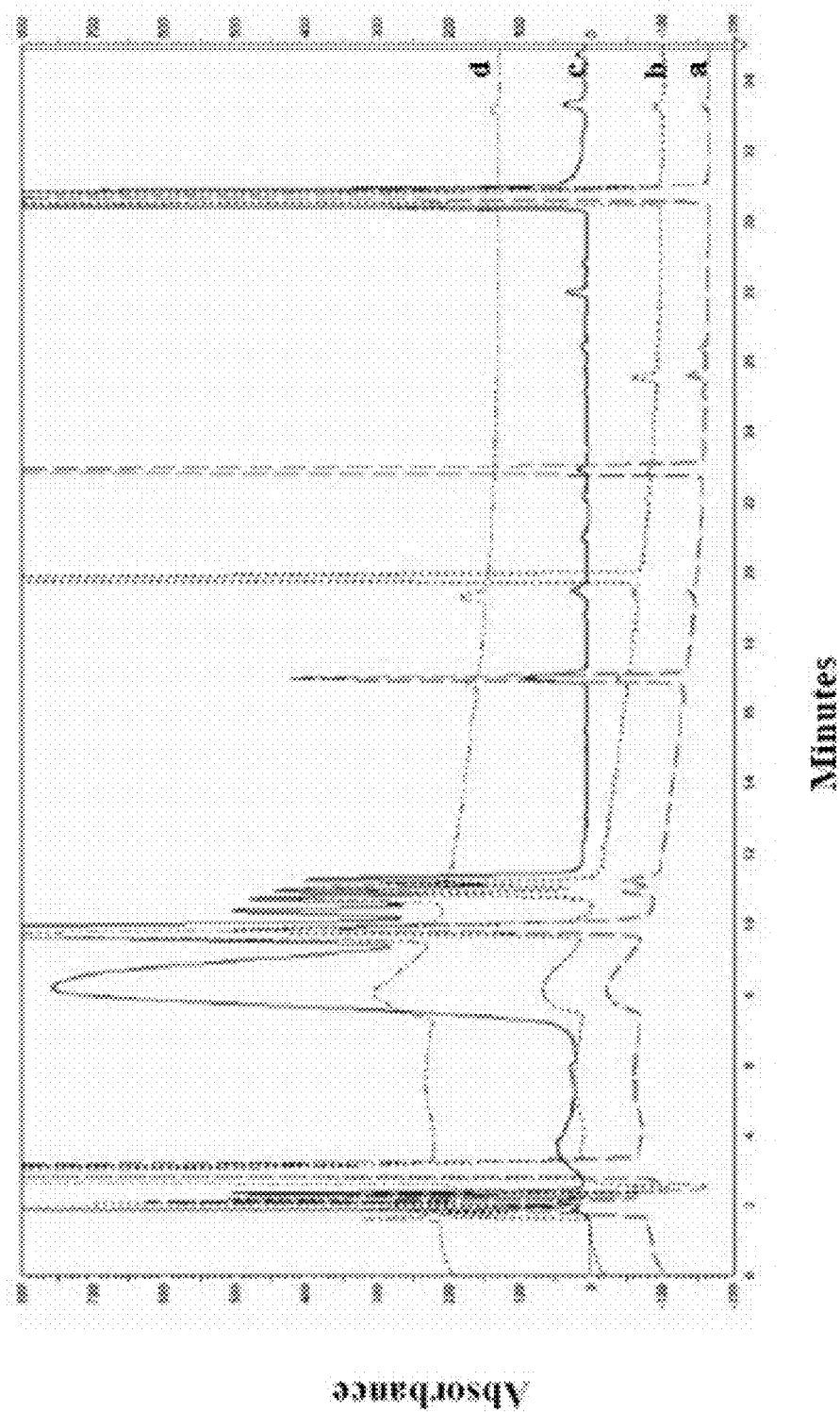
FIG. 15 shows HPLC analysis of FDVA of burkholdines emphasizing the presence of L-Ser-L-Asn residue. HPLC chromatogram of FDVA derivative of: (a) L-Ser-L-Asn (17 min), (b) L-Ser-D-Asn (19.7 min), (c) formic acid hydrolysate of burkholdines (17 min), (d) FDVA only.

Formic Acid Hydrolysis and Analysis. In 5 replicate microcentrifuge tubes, freshly prepared 2% formic acid (200 μl) was added to lyophilized burkholdines (50 μg). The tubes were heated to 108° C. in a dry heat block, with variable incubation times from 5 min to 1.5 h. Reactions were monitored by TLC (silica gel; 13:5:2 butanol:water:acetic acid) for presence of intermediate hydrolysis products. Upon completion the tubes were frozen and lyophilized to dryness. Standards of D-Asp-L-Ser and L-Asp-L-Ser were synthesized by the University of Utah DNA/Peptide Core Facility. Lyophilized formic acid hydrolysis products and the standards were then derivatized with 2,4-dinitro-1-fluorobenzene (DNB-F) and FDVA. For DNB-F derivatization, samples and standards were dissolved in borate buffer (40 μl; 100 mM at pH 9) and a solution of DNB-F (60 μl; 10 mM in acetonitrile). All mixtures were vortexed and heated at 65° C. for 30 min in a dry heat block and then allowed to cool. The DNB-F derivatives were separated by RP-HPLC using C18 column (4.6 mm×150 mm). A gradient of 5% acetonitrile/water to 80% for 30 min then to 95% for 40 min at 1 mL/min was used. The column was kept at 25° C. and the eluent was monitored at 230 nm (FIG. 14). The FDVA derivatization method was performed as described above.

Sugar Analysis for Bk-1229. Arabinose (3.3 mmol), xylose (3.3 mmol) and Bk-1229 (1.2 mmol) were lyophilized in silanized screw cap tubes and dessicated in vacuo over P$_2$O$_5$ for 3 days. 0.5 mL of 10% benzoyl chloride in pyridine (v/v) was added under nitrogen and the tubes were incubated at 37° C. for 10 h and then left at room temperature for 14 h. Each sample was diluted with 9 volumes of water and mixed by vortex for 1 min. O-perbenzoylated derivatives were purified on Bond-Elut C$_{18}$ disposable columns (Varian) and washed with water (6 mL), 25% acetonitrile-water (3 mL), 50% acetonitrile-water (3 mL) and 100% acetonitrile (3 mL). 100% acetonitrile fractions were dried and then dissolved in acetonitrile for HPLC analysis. The fractions were applied to a C$_{18}$ column (4.6 mm×150 mm) and eluted with acetonitrile-water 75%-100% over 20 min at 1 mL/min. The eluent was monitored at 230 nm (FIG. 14).

5. Biological Assays

The present compounds demonstrate potent antifungal activity against a broad spectrum of fungal species as demonstrated by the following examples.

a. Bioassay (In Vitro)

(1) Example 1

Anti-fungal activity for the present compounds was determined using microtitre format. Microtitre plates (96 wells: rows A-H, columns 1-12) were filled by the following protocol to give 2-fold serial dilutions of each of Bk-1229 and Bk-1097. Samples of Bk-1229 and Bk-1097 were dissolved in 1/10-strength BHIB containing 0.1% (w/v) dimethylsulfoxide (DMSO). Aliquots (50 μL) of 1/10-strength BHIB containing 0.1 (w/v) % DMSO (pH 7.4) were added to all wells except those in column 1. The wells in column 1 received 100 μL of the solutions of Bk-1229 or Bk-1097 and 50 μL was removed and mixed with the medium in the second well. This process was repeated through well 11, at which point an aliquot (50 μL) was removed and discarded. Well 12 was the blank (positive growth) control, BHIB+DMSO only. The test microorganisms employed in this example were *Saccharomyces cerevisiae*, *Candida albicans*, and *Aspergillus niger*, which were obtained from the Virginia Tech Microbiology Culture Collection. Cells of *S. cerevisiae* and *C. albicans* were grown in sterile 1/10-strength Brain Heart Infusion Broth (BHIB) and incubated at 30° C. for 18 h. Cells were counted as colony forming units on 1/10-strength BHIB agar. Spore suspensions of *A. niger* were prepared from lawns of sporulating colonies on 1/10-strength BHIB agar. The number of spores was determined by counting spores microscopically in a Petroff-Hauser counting chamber. The resulting culture or spore suspensions were diluted to $10^5$ cells or spores/mL. Following the preparation of the dilution series, 50 μL of microbial inocula ($10^5$/mL) were added to each well in a row. The concentration of Bk-1229 and Bk-1097 ranged from 50 to 0.05 μg/mL. After the plates were incubated at 30° C. for 4 days, measurement of minimal inhibitory concentration (MIC) results were read by comparing the turbidity (due to microbial growth) of each test well to the positive control wells. The measured MICs for each of burkholdines are summarized as follow:

TABLE 4

| Compound | MIC (µg/mL) | | |
|---|---|---|---|
| | S. cerevisiae | C. albicans | A. niger |
| Bk-1229 (1) | 0.4 | 12.5 | 12.5 |
| Bk-1097 (2) | 1.6 | 12.5 | 12.5 |
| Amphotericin B | 25 | 25 | 25 |

(2) Example 2

Contact petri dish studies were completed testing Dominion BioScience spray dried material against a list of plant diseases. The results are shown in Table 5. The experimental material (VBC80006) was prepared with 80% "formulated" heat-killed material Results (lowest rate) for complete inhibition with continuous exposure to spray dried material from Dominion BioScience against *Botrytis:* 20 ppm, *Mycosphaerella:* 100 ppm, *Cercospora:* 500 ppm, *Rhizoctonia:* 2000 ppm, *Sclerotinia*: >5000 ppm, *Pythium*: >5000 ppm, *Monilinia*: >5000 ppm, *Phytophthora* >2000 ppm. *Botrytis* was selected as the fungal pathogen for QC assays. Additional petridish assays and on-plant testing confirmed the activity on *Botrytis* of the produced material. Reduction in growth of *Alternaria* and *Colletotrichum* on exposure to the produced killed-microbial material was measured as well.

TABLE 5

Small scale in vitro assay results with various *Burkholderia* lab samples. Numbers are lowest PPM to obtain greater than 90% inhibition of plant disease spreading in petriplate. (NT = not tested). VBC 80% = VBC80006 (80% fermentation solids of *Burkholderia*)

| Plant Disease | DBS material | VBC 80% A.I | VBC 80% A.I., | VBC 80% A.I, |
|---|---|---|---|---|
| *Botrytis cin.* | 20 | 20-50 | NT | 400 |
| *Mycosphaerella* | 100 | NT | NT | NT |
| *Cercospora* | 500 | NT | NT | NT |
| *Rhizoctonia sol.* | 2000 | NT | NT | >2500 |
| *Monilinia* | >5000 | NT | NT | 1000 |
| *Sclerotinia scler.* | >5000 | NT | NT | >10000 |
| *Pythium* | >5000 | NT | NT | 10000 |
| *Phytophthora inf.* | >2000 | NT | NT | >5000 |
| *Alternaria alt.* | NT | NT | 500 | 500 |
| *Aspergillus ni.* | NT | NT | 500 | NT |
| *Pseudocercosporella* | NT | NT | 500 | NT |
| *Cladosporium clad.* | NT | NT | 500 | NT |
| *Penicillium fun.* | NT | NT | No effect | NT |
| *Chaetomium glo.* | NT | NT | 500 | NT |
| *Fusarium ox.* | NT | NT | 500 | >5000 |
| *Pyricularia or.* | NT | NT | NT | NT |
| *Erysiphe gram.* | NT | NT | NT | NT |
| *Spaerotheca ful.* | NT | NT | NT | NT |
| *Leptosphaeria nod.* | NT | NT | NT | NT |
| *Plasmopara vit.* | NT | NT | NT | NT |
| *Colletotrichum* | NT | NT | NT | 500 | b. Bioassay (In Vivo)

A lab study on individual grapes was performed to study the effects on *Botrytis* in more detail. Table 6 through Table 9 show the results of different application timing of VBC80006 after inoculation with *Botrytis*, different rates of VBC80006 as well as storage conditions of the grapes at either 21° C. or −5° C. In this example, the pathogen and compound were applied to the subject at the same time. The results show activity of VBC80006 to reduce decay development as well as the severity of decay (disease index=numeric system). A dose effect was visible when grapes were stored at 21° C. and the test scored at 5 days (end point). Three applications of VBC80006 at the higher dose appears to improve efficacy (Table 6). In Table 9 the results are shown of higher rates against a mixture of *Botrytis* and *Penicillium*.

TABLE 6

Laboratory study of control of *Botrytis* decay in table grapes. VBC80006 and *Botrytis* suspensions were applied at the same time.

| Treatment, rate applied and incubation temperature and time in days | Examination parameter | | | |
|---|---|---|---|---|
| | | | Decay Incidence | |
| | % Disease index | % Lesion area | 0 + 1 group* | 2 + 3 group* |
| VBC80006, 500 PPM, 21° C., 5 D | 76.2 | 18.4 | 21.5 | 78.5 |
| VBC80006, 5000 PPM, 21° C., 5 D | 41.3 | 7.3 | 64.5 | 35.5 |
| UTC | 92.0 | 50.8 | 8.0 | 92.0 |
| Non-inoculated | 0.7 | 0.0 | 100.0 | 0.0 |
| VBC80006, 500 PPM, −5° C., 21 D | 55.3 | 18.2 | 43.0 | 57.0 |
| VBC80006, 5000 PPM, −5° C., 21 D | 42.3 | 12.9 | 59.0 | 41.0 |
| UTC | 85.3 | 45.2 | 3.0 | 97.0 |
| Non-inoculated | 16.0 | 2.2 | 81.0 | 19.0 |

*3 = lesion > 3 mm with superficial fungal growth; 2 = lesion > 3 mm without superficial fungal growth; 1 = lesion < 3 mm with brown discoloration around pin-hole; 0 = no lesion or brown discoloration.

TABLE 7

Laboratory study of control of *Botrytis* decay in table grapes. VBC80006 suspension was applied at different times after *Botrytis* inoculation. Grapes were held for 5 days at 21° C.

| Treatment, rate, and treatment schedule | Examination parameter | | | |
|---|---|---|---|---|
| | | | Decay Incidence | |
| | % Disease index | % Lesion area | 0 + 1 group* | 2 + 3 group* |
| VBC80006, 500 PPM, immediately after inoculation | 76.0 | 21.0 | 28.0 | 72.0 |
| VBC80006, 500 PPM, 3 hrs after inoculation | 83.3 | 23.0 | 10.0 | 90.0 |
| VBC80006, 500 PPM, 24 hrs after inoculation | 82.0 | 17.0 | 14.0 | 86.0 |
| VBC80006, 500 PPM, immediate + 24 hrs + 48 hrs after inoculation | 63.3 | 12.7 | 34.0 | 66.0 |
| VBC80006, 5000 PPM, immediately after inoculation | 44.7 | 11.1 | 54.0 | 46.0 |
| VBC80006, 5000 PPM, 3 hrs after inoculation | 32.7 | 7.4 | 72.0 | 28.0 |
| VBC80006, 5000 PPM, 24 hrs after inoculation | 50.7 | 8.0 | 56.0 | 44.0 |
| VBC80006, 5000 PPM, immediately + 24 hrs + 48 hrs after inoculation | 37.3 | 2.9 | 76.0 | 24.0 |
| UTC | 92.0 | 50.8 | 8.0 | 92.0 |
| Non-inoculated | 0.7 | 0 | 100.0 | 0 |

TABLE 8

Laboratory study of control of *Botrytis* decay in table grapes.
VBC80006 suspension was applied at different times after *Botrytis*
inoculation.. Grapes were held for 21 days at −5° C.

| Treatment, rate, and treatment schedule | Examination parameter | | | |
|---|---|---|---|---|
| | % Disease index | % Lesion area | Decay Incidence | |
| | | | 0 + 1 group* | 2 + 3 group* |
| VBC80006, 500 PPM, immediately after inoculation | 58.0 | 20.3 | 40.0 | 60.0 |
| VBC80006, 500 PPM, 3 hrs after inoculation | 52.7 | 16.2 | 46.0 | 54.0 |
| VBC80006, 5000 PPM, immediately after inoculation | 48.7 | 14.6 | 52.0 | 48.0 |
| VBC80006, 5000 PPM, 3 hrs after inoculation | 36.0 | 11.1 | 66.0 | 34.0 |
| UTC | 84.0 | 45.1 | 4.0 | 96.0 |
| Non-inoculated | 15.3 | 2.3 | 82.0 | 18.0 |

TABLE 9

Laboratory study of control of both *Botrytis* and *Penicillium*
decay in table grapes. VBC80006 and *Botrytis* suspensions were
applied at the same time. Grapes were held for 5 days at 21° C.

| Treatment, rate applied | Examination parameter | | | |
|---|---|---|---|---|
| | % Disease index | % Lesion area | Decay Incidence | |
| | | | 0 + 1 group* | 2 + 3 group* |
| VBC80006, 2500 PPM | 36.2 | 3.7 | 71.1 | 28.9 |
| VBC80006, 5000 PPM | 28.5 | 1.9 | 78.9 | 21.1 |
| Fungicide reference | 18.2 | 0.3 | 96.7 | 3.3 |
| UTC | 91.1 | 26.8 | 8.9 | 91.1 |

In one example, banana leaves were innoculated with black sigatoka disease (*Mycosphaerella*), Table 10 and 11 show inhibition of spore germination and germ tube growth of the disease.

TABLE 10

In vivo study on banana leaves with black Sigatoka
(*Mycosphaerella fijiensis*). Germ tube inhibition
as percentage of check. VBC80006 is 80% fermentation
solids of *Burkholderia*.

| Treatment | % Germ tube inhibition | | | | | |
|---|---|---|---|---|---|---|
| | 0.01 PPM | 0.1 PPM | 1.0 PPM | 10.0 PPM | 100.0 PPM | EC50* |
| VBC80006 | 23.5 | 9.0 | 16.0 | 85.0 | 100.0 | 30 PPM |

*EC50 = concentration in PPM required for 50% inhibition.

TABLE 11

In vivo study on banana leaves with black Sigatoka
(*Mycosphaerella fijiensis*). Inhibition of spore germination.
VBC80006 is 80% fermentation of solids of
*Burkholderia*.

| Treatment | % of non-germinating spores | | | | | |
|---|---|---|---|---|---|---|
| | Check | 0.01 PPM | 0.1 PPM | 1.0 PPM | 10.0 PPM | 100.0 PPM |
| VBC80006 | 0 | 17 | 0 | 0 | 50.0 | 100.0 | c. Field Evaluations

In one example, *Burkholderia* killed-microbial material (VBC80006) was tested on banana trees to evaluate the antifungal activity against black sikatoga disease. The produced *Burkholderia* killed-microbial material (VBC80006) sprayed in an oil-in-water emulsion reduced the incidence of black Sigatoka especially on the lower part of banana leaves as good as DiThane over a 46 day exposure to natural infestation. (See Table 12).

TABLE 12

In vivo study on banana leaves with black Sigatoka (*Mycosphaerella
fijiensis*). Inhibition of disease severity by VBC80006. Applications
made with airbrush at equivalent of 23 liters per ha spray volume,
and using as spreader sticker Spraytex oil at 7 liter/ha plus NP 7
at 1% the rate of the oil. One application, treatments replicated
6X in RCB design. Natural levels of disease pressure.

| Treatment | Side of leaf | Disease Severity (days after application) | | |
|---|---|---|---|---|
| | | 25 days | 40 days | 46 days |
| VBC80006, 100 PPM | Upper surface | 6 | 28 | 41 |
| VBC80006, 1000 PPM | Upper surface | 3 | 31 | 61 |
| VBC80006, 2500 PPM | Upper surface | 0 | 34 | 68 |
| DiThane | Upper surface | 0 | 36 | 74 |
| UTC | Upper surface | 0 | 68 | 96 |
| VBC80006, 100 PPM | Lower surface | 0 | 6 | 27 |
| VBC80006, 1000 PPM | Lower surface | 0 | 7 | 8 |
| VBC80006, 2500 PPM | Lower surface | 0 | 4 | 7 |
| DiThane | Lower surface | 0 | 4 | 9 |
| UTC | Lower surface | 0 | 49 | 84 |

Limited field tests of the *Burkholderia* killed-microbial material So far limited field tests of the *Burkholderia* killed-microbial material did not show any efficacy in the reduction of the plant diseases such as *Pythium*. Greenhouse and on-leaf assays showed promise in a few cases. On-plant assays done confirmed activity of VBC80006 on *Botrytis* at 200 PPM. Other tests showed moderate activity against *Rhizoctonia*: 5000 ppm, *Sclerotinia*: 5000 ppm, *Phytophthora* 5000 ppm, *Alternaria*: 5000 ppm, *Fusarium*: 1000 ppm, *Pyricularia*: 1000 ppm, *Erysiphe*: 5000 ppm, *Spaerotheca*: 5000 ppm, *Leptosphaeria*: 1000 ppm, *Plasmopara:* 5000 ppm.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An isolated compound having a structure represented by a formula:

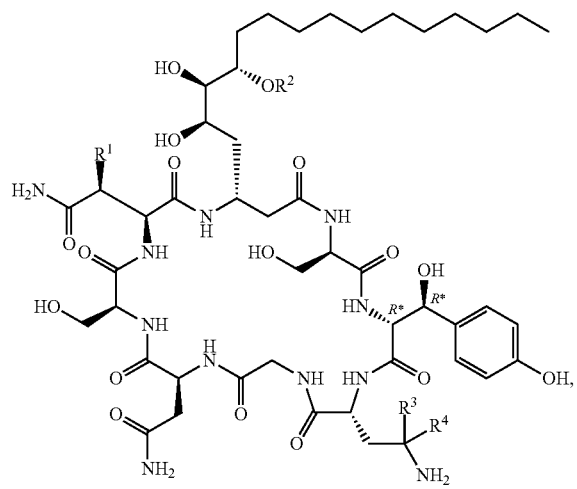

wherein $R^1$ is hydrogen or hydroxyl;
wherein $R^2$ is hydrogen or xylose; and
wherein $R^3$ and $R^4$ are each hydrogen or together oxygen, or a pharmaceutically acceptable salt thereof.

2. The compound of claim 1, wherein $R^3$ and $R^4$ are each hydrogen.
3. The compound of claim 1, wherein $R^3$ and $R^4$ are together oxygen.
4. The compound of claim 1, wherein $R^1$ is hydrogen.
5. The compound of claim 1, wherein $R^1$ is hydroxyl.
6. The compound of claim 1, wherein $R^2$ is hydrogen.
7. The compound of claim 1, wherein $R^2$ has a structure represented by a formula:

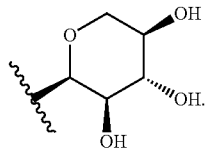 [SMILES: *[C@H]1OC[C@@H](O)[C@H](O)[C@H]1O]

8. The compound of claim 1, wherein $R^2$ has a structure represented by a formula:

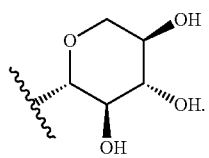 [SMILES: *[C@@H]1OC[C@@H](O)[C@H](O)[C@H]1O]

9. The compound of claim 1, wherein the compound exhibits inhibition of fungal growth with a MIC of less than about 12.5 µg/ml against *Aspergillus*.
10. The compound of claim 1, wherein the compound exhibits of about at least 90% inhibition of fungal growth with an IC of less than about 2000 ppm against *Botrytis*.
11. The compound of claim 1, wherein the compound is cytotoxic.
12. The compound of claim 1, wherein the compound exhibits antifungal activity against *Aspergillus, Botrytis, Cercospora, Cercosporidium, Erysiphe, Geotrichum, Mycosphaerella, Mucor, Penicillium, Phoma, Phytophthora, Plasmopora, Pseudopeziza, Puccinia, Pythium, Rhizoctonia, Rhizopus, Septoria, Sporothrix, Stemphylium, Trichophyton,* or *Verticillium*.
13. The compound of claim 1, wherein the compound is isolated from a culture of *Burkholderia ambifaria*.
14. A pharmaceutical composition comprising a compound having a structure represented by a formula:

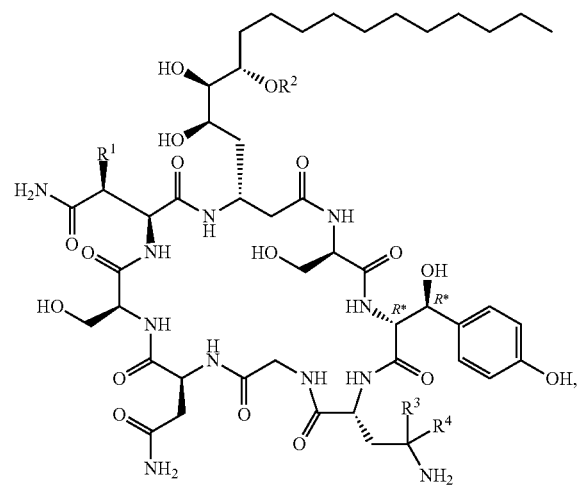

wherein $R^1$ is hydrogen or hydroxyl; wherein $R^2$ is hydrogen or xylose; and wherein $R^3$ and $R^4$ are each hydrogen or together oxygen, or a pharmaceutically acceptable salt thereof, and
a pharmaceutically acceptable carrier.

15. The pharmaceutical composition of claim 1, wherein $R^3$ and $R^4$ are together oxygen.
16. The pharmaceutical composition of claim 1, wherein $R^1$ is hydroxyl.
17. The pharmaceutical composition of claim 1, wherein $R^2$ is hydrogen.
18. The pharmaceutical composition of claim 1, wherein $R^2$ is xylose.
19. An agricultural composition comprising a compound having a structure represented by a formula:

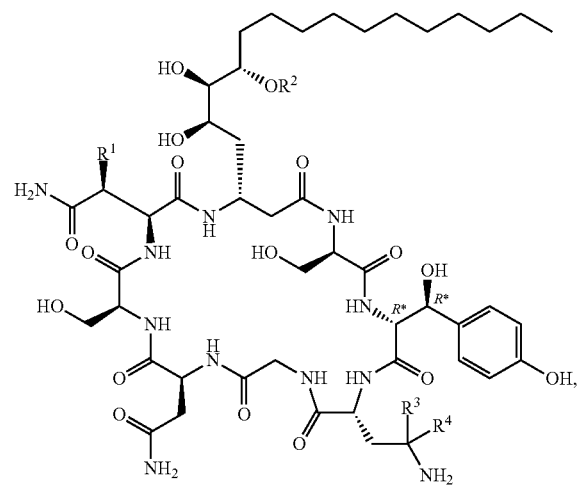

wherein $R^1$ is hydrogen or hydroxyl; wherein $R^2$ is hydrogen or xylose; and wherein $R^3$ and $R^4$ are each hydrogen or together oxygen, or a pharmaceutically acceptable salt thereof, and
an agriculturally acceptable carrier.

20. The agricultural composition of claim 1, wherein $R^3$ and $R^4$ are together oxygen.

21. The agricultural composition of claim 1, wherein $R^1$ is hydroxyl.

22. The agricultural composition of claim 1, wherein $R^2$ is hydrogen.

23. The agricultural composition of claim 1, wherein $R^2$ is xylose.

* * * * *